United States Patent
Wurtzel et al.

(10) Patent No.: US 10,913,959 B2
(45) Date of Patent: *Feb. 9, 2021

(54) METHOD FOR ISOMERIZING DOUBLE BONDS

(71) Applicant: Research Foundation of the City University of New York, New York, NY (US)

(72) Inventors: Eleanore T. Wurtzel, Riverdale, NY (US); Jesús Beltrán, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/032,454

(22) Filed: Jul. 11, 2018

(65) Prior Publication Data

US 2018/0312877 A1 Nov. 1, 2018

Related U.S. Application Data

(63) Continuation of application No. 15/169,894, filed on Jun. 1, 2016, now Pat. No. 10,036,042.

(60) Provisional application No. 62/168,994, filed on Jun. 1, 2015.

(51) Int. Cl.
    *C12N 9/90* (2006.01)
    *C12P 5/02* (2006.01)
    *C12P 23/00* (2006.01)
    *C12P 5/00* (2006.01)

(52) U.S. Cl.
    CPC .............. *C12P 5/026* (2013.01); *C12N 9/90* (2013.01); *C12P 5/007* (2013.01); *C12P 23/00* (2013.01); *C12Y 502/01012* (2013.01)

(58) Field of Classification Search
    None
    See application file for complete search history.

(56) References Cited

PUBLICATIONS

Beltran et al. ("Control of carotenoid biosynthesis through a heme-based cis-trans isomerase," Nature Chem. Biol. Jun. 15, 2015, 11, 598-605.*
Chen et al., Isolation and Characterization of the Z-ISO Gene Encoding a Missing Component of Carotenoid Biosynthesis in Plants, Plant Physiology, 2010, 153, 66-79.*
Novagen, Duet vctors, User Protocol TB340 Rev. F 0211JN, 2011.*
Beltran, J. et al.; Control of carotenoid biosynthesis through a heme-based cis-trans isomerase; Natural Chemical Biology; Jun. 15, 2015; pp. 1-23; doi: 10.1038/nchembio.1840; Advance online publication.
Chen, Y. et al.; Isolation and Characterization of the Z-ISO Gene Encoding a Missing Component of Carotenoid Biosynthesis in Plants; Plant Physiology; May 2010; pp. 66-79; vol. 153; American Society of Plant Biologists.
Li, F. et al.; Maize Y9 Encodes a Product Essential for 15-cis-zeta-Carotene Isomerization; Plant Physiology; Jun. 2007; pp. 1181-1189; vol. 144; American Society of Plant Biologists.
Heipieper, H. et al.; The cis-trans isomerase of unsaturated fatty acids in Pseudomonas and Vibri: biochemistry, molecular biology and physiological function of a unique stress adaptive mechanism; FEMS Microbiology Letters; Nov. 7, 2003; pp. 1-7; 229.
Uniprot; Accession No. A0A078EAW1; 2014; www.uniprot.org.
Holtwick, R. et al.; cis/trans Isomerase of Unsaturated Fatty Acids of Pseudomonas putida P8: Evidence for a Heme Protein of the Cytochrome c Type; Applied and Envioronmental Microbiology, Jun. 1999; pp. 2644-2649; vol. 65, No. 6.
Okuyama, H. et al.; Purification and characterization of 9-hexadecenoic acid cis-trans isomerase from *Pseudomonas* sp. strain E-3; Arch. Microbiol; 1998; pp. 29-35; 169.

* cited by examiner

*Primary Examiner* — Robert B Mondesi
*Assistant Examiner* — Todd M Epstein
(74) *Attorney, Agent, or Firm* — Peter J. Mikesell; Schmeiser, Olsen & Watts, LLP

(57) ABSTRACT

A method for isomerizing a double bond is provided. A substrate is exposed to an isomerase enzyme, wherein the isomerase enzyme comprises a redox-regulated ligand switch and heme b cofactor. A reducing agent changes iron (III) to iron (II). The enzyme isomerizes double bonds in the iron (II) state but not in the iron (III) state. In one embodiment, the enzyme is homologous with 15-cis-ζ-carotene isomerase (Z-ISO).

2 Claims, 21 Drawing Sheets

Specification includes a Sequence Listing.

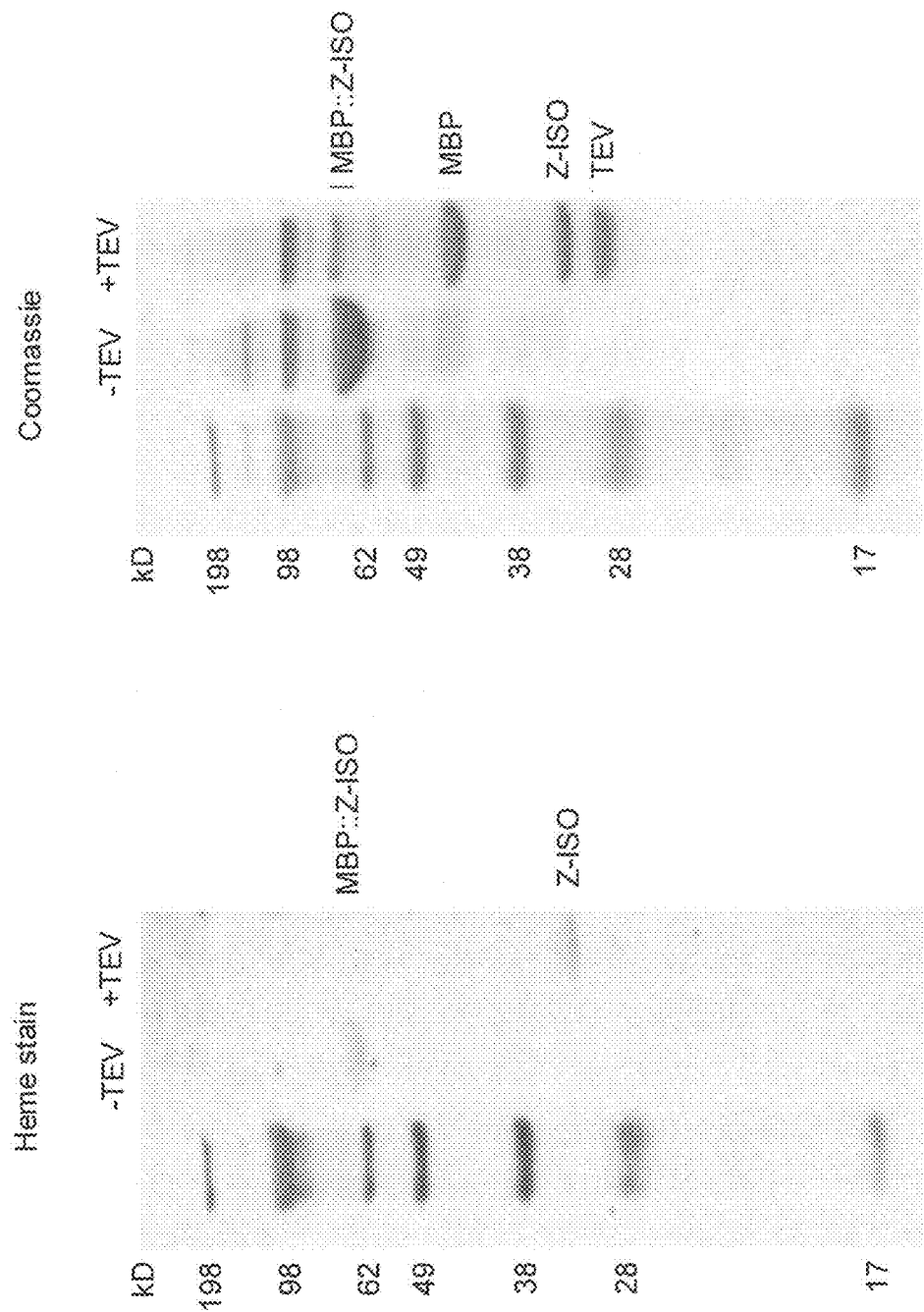

GAGCTC<u>at</u>ggcgagccagctgcgtctgcatctggcggcgacccccgccgctgctgccgcatcgtcgt
ccgcatctgccgcgtccgctgtgcccgaccctgaacccgattcgtgcgccgctgccgccgctgagccgt
gtgctgagccatgcgcgtccggcgcgtgcggtgggcggcggcattgaaccgaaagaaggcgtggtgg
cggaaggcgatgaaagcggcggcggcccggtgctggtgggcgaagatagcgcggcgtttgaactga
aagatcagagcgtggcgagctgggcgtattttgcgggcattctgggcgcggtgctggtggcgctgaacg
tgctggtgattgatccgagcaccggcgtgggcaccaaatttctggatgcggtggcgagcgtgagcgata
gccatgaagtggtgatgctgctgctgaccattattttttgcggtggtgcatagcggcatggcgagcctgcgtg
aaagcggcgaaaaaattgtgggcgaacgtgtgtatcgtgtgctgtttgcgggcattagcctgccgctggc
ggtgaccaccattgtgtattttattaaccatcgttatgatggcacccagctgtggcaggtgcagggcattac
cggcattcatgaactgctgtggtttagcagctttattagctttttttttctgtatccgagcacctttaacctgctgg
aagtggcggcggtggataaaccgaaactgcatatgtgggaaaccggcattatgcgtattacccgtcatc
cgcagatggtgggccaggtgatttggtgcctggcgcataccctgtggattggcaatagcgtggcggtggc
ggcgagcgtgggcctgattagccatcatctgtttggcgcgtggaacggcgatcgtcgtctgctgagccgtt
atggcgaagcgtttgaagtgctgaaaaaacgtaccagcgtgatgccgtttgcggcgattattgatggccg
tcagaaactgccgaaagattatcataaagaattttttcgtctgccgtatgtggcgattaccatgctgaccctg
ggcgcgtattttgcgcatccgctgatgcaggcgagcagctatcagctgccgtggtaaGGATCC
(SEQ ID NO: 13)

<u>MASQLRLHLAATPPLLPHRRPHLPRPLCPTLNPIRAPLPPLSRVLSHARPA
RAVGGGIEPKEGVVAEGDESGGGPVLVGEDSAAFELKDQSVASWAYFA
GILGAVLVALNVLWIDPSTGVGTKFLDAVASVSDSHEVVMLLLTIIFAVVHS
GMASLRESGEKIVGERVYRVLFAGISLPLAVTTIVYFINHRYDGTQLWQVQ
GITGIHELLWFSSFISFFFLYPSTFNLLEVAAVDKPKLHMWETGIMRITRHP
QMVGQVIWCLAHTLWIGNSVAVAASVGLISHHLFGAWNGDRRLLSRYGE
AFEVLKKRTSVMPFAAIIDGRQKLPKDYHKEFFRLPYVAITMLTLGAYFAHP
LMQASSYQLPW</u> (SEQ ID NO: 12)

SEQUENCE LISTING

```
<160> NUMBER OF SEQ ID NOS: 13

<210> SEQ ID NO 1
<211> LENGTH: 40
<212> TYPE: DNA
<213> ORGANISM: Artificial Sequence
<220> FEATURE:
<223> OTHER INFORMATION: Completely synthetic forward primer for PCR

<400> SEQUENCE: 1
tacttccaat ccaatgccat gcgtccggcg cgtgcggtgg                             40

<210> SEQ ID NO 2
<211> LENGTH: 38
<212> TYPE: DNA
<213> ORGANISM: Artificial Sequence
<220> FEATURE:
<223> OTHER INFORMATION: Completely synthetic reverse sequence for PCR

<400> SEQUENCE: 2
ttatccactt ccaatgctac cagggaagtt ggtagctg                              38

<210> SEQ ID NO 3
<211> LENGTH: 34
<212> TYPE: DNA
<213> ORGANISM: Artificial Sequence
```

-continued

```
<220> FEATURE:
<223> OTHER INFORMATION: Completely synthetic forward sequence for use
      in PCR

<400> SEQUENCE: 3
atctctagaa tggcctccca gctccgcctc cacc                                 34

<210> SEQ ID NO 4
<211> LENGTH: 33
<212> TYPE: DNA
<213> ORGANISM: Artificial Sequence
<220> FEATURE:
<223> OTHER INFORMATION: Completely synthetic reverse sequence for PCR

<400> SEQUENCE: 4
atcggatccc cagggaagtt ggtagctgga tgc                                  33

<210> SEQ ID NO 5
<211> LENGTH: 24
<212> TYPE: DNA
<213> ORGANISM: Artificial Sequence
<220> FEATURE:
<223> OTHER INFORMATION: Completely synthetic forward primer for use in
      PCR.

<400> SEQUENCE: 5
ccacctgcag aattctatgg cctc                                            24

<210> SEQ ID NO 6
<211> LENGTH: 54
<212> TYPE: DNA
<213> ORGANISM: Artificial Sequence
<220> FEATURE:
<223> OTHER INFORMATION: Completely synethic reverse sequence for use in
      PCR

<400> SEQUENCE: 6
gtctctagat tattttcaa attgaggatg agaccaccag ggaagttggt agct            54

<210> SEQ ID NO 7
<211> LENGTH: 30
<212> TYPE: DNA
<213> ORGANISM: Artificial Sequence
<220> FEATURE:
<223> OTHER INFORMATION: Completely synthetic forward primer for use in
      PCR.

<400> SEQUENCE: 7
cgggatcctc acgctcgtcc cgcccgtgcg                                      30

<210> SEQ ID NO 8
<211> LENGTH: 29
<212> TYPE: DNA
<213> ORGANISM: Artificial Sequence
<220> FEATURE:
<223> OTHER INFORMATION: Completely synthetic reverse primer for use in
      PCR.

<400> SEQUENCE: 8
gcgtcgacct accagggaag ttggtagct                                       29

<210> SEQ ID NO 9
<211> LENGTH: 367
<212> TYPE: PRT
<213> ORGANISM: Arabidopsis thaliana

<400> SEQUENCE: 9
```

```
Met Ala Val Tyr His Leu Leu Leu Ser Ser Pro Pro Ser Leu Leu Leu
1               5                   10                  15

Leu Pro Pro Ser Pro Arg Arg Pro Asn Leu Thr Leu Ile Arg Arg Ile
            20                  25                  30

Pro Ala His Pro Arg Leu Gly Asn Ser Thr Ser Leu Leu Ser Ser Ser
        35                  40                  45

Ser Pro Val Ile Arg Lys Ile Leu Val Arg Ser Thr Leu Arg Glu Asp
50                  55                  60

Gln Pro Ile Ala Ser Asp Ser Glu Ser Ser Pro Thr Leu Leu Ile Gly
65                  70                  75                  80

Glu Asp Ser Ala Ala Phe Glu Leu Gly Lys Gln Lys Leu Val Ser Trp
                85                  90                  95

Val Tyr Phe Gly Val Val Leu Gly Val Val Leu Phe Ile Leu Asn Val
            100                 105                 110

Val Trp Ile Asp Asn Ser Thr Gly Phe Gly Lys Ser Phe Ile Asp Ala
        115                 120                 125

Val Ser Asn Ile Ser Gly Ser Pro Glu Val Ala Met Leu Met Leu Ile
130                 135                 140

Leu Ile Phe Ala Ile Val His Ser Gly Leu Ala Ser Leu Arg Asp Ile
145                 150                 155                 160

Gly Glu Lys Leu Ile Gly Glu Arg Ala Phe Arg Val Leu Phe Ala Gly
                165                 170                 175

Ile Ser Leu Pro Leu Ala Met Ser Thr Ile Val Tyr Phe Ile Asn His
            180                 185                 190

Arg Tyr Asp Gly Ser Gln Leu Trp Gln Leu Gln Gly Val Pro Gly Val
        195                 200                 205

His Glu Ala Ile Trp Val Ala Asn Phe Val Ser Phe Phe Leu Tyr
210                 215                 220

Pro Ser Thr Phe Asn Leu Leu Glu Val Ala Ala Val Asp Lys Pro Lys
225                 230                 235                 240

Met His Leu Trp Glu Thr Gly Ile Met Arg Ile Thr Arg His Pro Gln
                245                 250                 255

Met Val Gly Gln Ile Val Trp Cys Leu Ala His Thr Leu Trp Ile Gly
            260                 265                 270

Asn Thr Val Ala Ala Ser Ala Ser Leu Gly Leu Ile Ala His His Leu
        275                 280                 285

Phe Gly Ala Trp Asn Gly Asp Arg Arg Leu Ala Lys Arg Tyr Gly Glu
290                 295                 300

Asp Phe Glu Ser Ile Lys Lys Arg Thr Ser Val Ile Pro Phe Ala Ala
305                 310                 315                 320

Ile Phe Glu Gly Arg Gln Val Leu Pro Glu Asp Tyr Tyr Lys Glu Phe
                325                 330                 335

Val Arg Leu Pro Tyr Leu Ala Ile Thr Ala Leu Thr Val Gly Ala Tyr
            340                 345                 350

Phe Ala His Pro Leu Met Gln Gly Ala Ser Phe Arg Leu His Trp
        355                 360                 365

<210> SEQ ID NO 10
<211> LENGTH: 285
<212> TYPE: PRT
<213> ORGANISM: Arabidopsis thaliana

<400> SEQUENCE: 10

Met Ala Val Tyr His Leu Leu Leu Ser Ser Pro Pro Ser Leu Leu Leu
```

```
1               5                   10                  15
Leu Pro Pro Ser Pro Arg Arg Pro Asn Leu Thr Leu Ile Arg Arg Ile
                20                  25                  30

Pro Ala His Pro Arg Leu Gly Asn Ser Thr Ser Leu Leu Ser Ser Ser
                35                  40                  45

Ser Pro Val Ile Arg Lys Ile Leu Val Arg Ser Thr Leu Arg Glu Asp
                50                  55                  60

Gln Pro Ile Ala Ser Asp Ser Glu Ser Ser Pro Thr Leu Leu Ile Gly
65                              70                  75                  80

Glu Asp Ser Ala Ala Phe Glu Leu Gly Lys Gln Lys Leu Val Ser Trp
                            85                  90                  95

Val Tyr Phe Gly Val Val Leu Gly Val Val Leu Phe Ile Leu Asn Val
                100                 105                 110

Val Trp Ile Asp Asn Ser Thr Gly Phe Gly Lys Ser Phe Ile Asp Ala
                115                 120                 125

Val Ser Asn Ile Ser Gly Ser Pro Glu Val Ala Met Leu Met Leu Ile
                130                 135                 140

Leu Ile Phe Ala Ile Val His Ser Gly Leu Ala Ser Leu Arg Asp Ile
145                 150                 155                 160

Gly Glu Lys Leu Ile Gly Glu Arg Ala Phe Arg Val Leu Phe Ala Gly
                165                 170                 175

Ile Ser Leu Pro Leu Ala Met Ser Thr Ile Val Tyr Phe Ile Asn His
                180                 185                 190

Arg Tyr Asp Gly Ser Gln Leu Trp Gln Leu Gln Gly Val Pro Gly Val
                195                 200                 205

His Glu Ala Ile Trp Val Ala Asn Phe Val Ser Phe Phe Leu Tyr
210                 215                 220

Pro Ser Thr Phe Asn Leu Leu Glu Val Ala Ala Val Asp Lys Pro Lys
225                 230                 235                 240

Met His Leu Trp Glu Thr Gly Ile Met Arg Ile Thr Arg His Pro Gln
                245                 250                 255

Val Leu Asn Ile Ser Leu Met Cys Leu Asn Met Lys Thr Ile Ser Phe
                260                 265                 270

Ile Phe Val Phe Gln Lys Tyr Arg Lys Ile Gly Phe Leu
                275                 280                 285

<210> SEQ ID NO 11
<211> LENGTH: 256
<212> TYPE: PRT
<213> ORGANISM: Arabidopsis thaliana

<400> SEQUENCE: 11

Met Ala Val Tyr His Leu Leu Ser Ser Pro Pro Ser Leu Leu Leu
1               5                   10                  15

Leu Pro Pro Ser Pro Arg Arg Pro Asn Leu Thr Leu Ile Arg Arg Ile
                20                  25                  30

Pro Ala His Pro Arg Leu Gly Asn Ser Thr Ser Leu Leu Ser Ser Ser
                35                  40                  45

Ser Pro Val Ile Arg Lys Ile Leu Val Arg Ser Thr Leu Arg Glu Asp
                50                  55                  60

Gln Pro Ile Ala Ser Asp Ser Glu Ser Ser Pro Thr Leu Leu Ile Gly
65                              70                  75                  80

Glu Asp Ser Ala Ala Phe Glu Leu Gly Lys Gln Lys Leu Val Ser Trp
                            85                  90                  95
```

```
Val Tyr Phe Gly Val Val Leu Gly Val Val Leu Phe Ile Leu Asn Val
            100                 105                 110

Val Trp Ile Asp Asn Ser Thr Gly Phe Gly Lys Ser Phe Ile Asp Ala
        115                 120                 125

Val Ser Asn Ile Ser Gly Ser Pro Glu Val Ala Met Leu Met Leu Ile
    130                 135                 140

Leu Ile Phe Ala Ile Val His Ser Gly Leu Ala Ser Leu Arg Asp Ile
145                 150                 155                 160

Gly Glu Lys Leu Ile Gly Glu Arg Ala Phe Arg Val Leu Phe Ala Gly
                165                 170                 175

Ile Ser Leu Pro Leu Ala Met Ser Thr Ile Val Tyr Phe Ile Asn His
            180                 185                 190

Arg Tyr Asp Gly Ser Gln Leu Trp Gln Leu Gln Gly Val Pro Gly Val
        195                 200                 205

His Glu Ala Ile Trp Val Ala Asn Phe Val Ser Phe Phe Leu Tyr
    210                 215                 220

Pro Ser Thr Phe Asn Leu Leu Glu Val Ala Ala Val Asp Lys Pro Lys
225                 230                 235                 240

Met His Leu Trp Glu Thr Gly Ile Met Arg Ile Thr Arg His Pro Gln
                245                 250                 255

<210> SEQ ID NO 12
<211> LENGTH: 366
<212> TYPE: PRT
<213> ORGANISM: Zea mays

<400> SEQUENCE: 12

Met Ala Ser Gln Leu Arg Leu His Leu Ala Ala Thr Pro Pro Leu Leu
1               5                   10                  15

Pro His Arg Arg Pro His Leu Pro Arg Pro Leu Cys Pro Thr Leu Asn
            20                  25                  30

Pro Ile Arg Ala Pro Leu Pro Pro Leu Ser Arg Val Leu Ser His Ala
        35                  40                  45

Arg Pro Ala Arg Ala Val Gly Gly Gly Ile Glu Pro Lys Glu Gly Val
    50                  55                  60

Val Ala Glu Gly Asp Glu Ser Gly Gly Gly Pro Val Leu Val Gly Glu
65                  70                  75                  80

Asp Ser Ala Ala Phe Glu Leu Lys Asp Gln Ser Val Ala Ser Trp Ala
                85                  90                  95

Tyr Phe Ala Gly Ile Leu Gly Ala Val Leu Ala Leu Asn Val Leu
            100                 105                 110

Trp Ile Asp Pro Ser Thr Gly Val Gly Thr Lys Phe Leu Asp Ala Val
        115                 120                 125

Ala Ser Val Ser Asp Ser His Glu Val Val Met Leu Leu Leu Thr Ile
    130                 135                 140

Ile Phe Ala Val Val His Ser Gly Met Ala Ser Leu Arg Glu Ser Gly
145                 150                 155                 160

Glu Lys Ile Val Gly Glu Arg Val Tyr Arg Val Leu Phe Ala Gly Ile
                165                 170                 175

Ser Leu Pro Leu Ala Val Thr Thr Ile Val Tyr Phe Ile Asn His Arg
            180                 185                 190

Tyr Asp Gly Thr Gln Leu Trp Gln Val Gln Gly Ile Thr Gly Ile His
        195                 200                 205

Glu Leu Leu Trp Phe Ser Ser Phe Ile Ser Phe Phe Leu Tyr Pro
    210                 215                 220
```

```
Ser Thr Phe Asn Leu Leu Glu Val Ala Ala Val Asp Lys Pro Lys Leu
225                 230                 235                 240

His Met Trp Glu Thr Gly Ile Met Arg Ile Thr Arg His Pro Gln Met
                245                 250                 255

Val Gly Gln Val Ile Trp Cys Leu Ala His Thr Leu Trp Ile Gly Asn
            260                 265                 270

Ser Val Ala Val Ala Ala Ser Val Gly Leu Ile Ser His His Leu Phe
        275                 280                 285

Gly Ala Trp Asn Gly Asp Arg Arg Leu Leu Ser Arg Tyr Gly Glu Ala
290                 295                 300

Phe Glu Val Leu Lys Lys Arg Thr Ser Val Met Pro Phe Ala Ala Ile
305                 310                 315                 320

Ile Asp Gly Arg Gln Lys Leu Pro Lys Asp Tyr His Lys Glu Phe Phe
                325                 330                 335

Arg Leu Pro Tyr Val Ala Ile Thr Met Leu Thr Leu Gly Ala Tyr Phe
            340                 345                 350

Ala His Pro Leu Met Gln Ala Ser Ser Tyr Gln Leu Pro Trp
        355                 360                 365

<210> SEQ ID NO 13
<211> LENGTH: 1113
<212> TYPE: DNA
<213> ORGANISM: Artificial Sequence
<220> FEATURE:
<223> OTHER INFORMATION: Maize Z-ISO codon optimized for E. coli

<400> SEQUENCE: 13
gagctcatgg cgagccagct gcgtctgcat ctggcggcga ccccgccgct gctgccgcat      60
cgtcgtccgc atctgccgcg tccgctgtgc ccgaccctga accgattcg tgcgccgctg     120 ccgccgctga gccgtgtgct gagccatgcg cgtccggcgc gtgcggtggg cggcggcatt     180
gaaccgaaag aaggcgtggt ggcggaaggc gatgaaagcg cggcggcccc ggtgctggtg     240
ggcgaagata gcgcggcgtt tgaactgaaa gatcagagcg tggcgagctg gcgtatttt     300 gcgggcattc tgggcgcggt gctggtggcg ctgaacgtgc tgtggattga tccgagcacc     360
ggcgtgggca ccaaatttct ggatgcggtg gcgagcgtga gcgatagcca tgaagtggtg     420
atgctgctgc tgaccattat ttttgcggtg gtgcatagcg gcatggcgag cctgcgtgaa     480
agcggcgaaa aaattgtggg cgaacgtgtg tatcgtgtgc tgtttgcggg cattagcctg     540
ccgctggcgg tgaccaccat tgtgtatttt attaaccatc gttatgatgg cacccagctg     600
tggcaggtgc agggcattac cggcattcat gaactgctgt ggtttagcag ctttattagc     660
tttttttttc tgtatccgag caccttttaac ctgctggaag tggcggcggt ggataaaccg     720
aaactgcata tgtgggaaac cggcattatg cgtattaccc gtcatccgca gatggtgggc     780
caggtgattt ggtgcctggc gcatacccty tggattggca atagcgtggc ggtggcggcg     840
agcgtgggcc tgattagcca tcatctgttt ggcgcgtgga acggcgatcg tcgtctgctg     900
agccgttatg gcgaagcgtt tgaagtgctg aaaaaacgta ccagcgtgat gccgtttgcg     960
gcgattattg atggccgtca gaaactgccg aaagattatc ataaagaatt ttttcgtctg    1020
ccgtatgtgg cgattaccat gctgaccctg ggcgcgtatt ttgcgcatcc gctgatgcag    1080
gcgagcagct atcagctgcc gtggtaagga tcc                                 1113
```

METHOD FOR ISOMERIZING DOUBLE BONDS

CROSS-REFERENCE TO RELATED APPLICATIONS

This application is a continuation of U.S. patent application Ser. No. 15/169,894 (filed Jun. 1, 2016) which claims priority to and is a non-provisional of U.S. Patent Application Ser. No. 62/168,994 (filed Jun. 1, 2015), the entirety of which are incorporated herein by reference.

STATEMENT OF FEDERALLY SPONSORED RESEARCH OR DEVELOPMENT

This invention was made with government support under contract number GM081160 awarded by the National Institute of Health (NIH). The government has certain rights in the invention.

REFERENCE TO A SEQUENCE LISTING

This application refers to a "Sequence Listing" listed below, which is provided as an electronic document entitled "Sequence_ST25.txt" (10 kb, created on May 18, 2016), which is incorporated herein by reference in its entirety.

BACKGROUND OF THE INVENTION

The subject matter disclosed herein relates to methods for isomerizing double bonds using enzymatic catalysts. Plants synthesize carotenoids, which are essential metabolites for plant development and survival. These metabolites also serve as essential nutrients for human health. The biosynthetic pathway for all plant carotenoids occurs in chloroplasts and other plastids and requires 15-cis-ζ-carotene isomerase (Z-ISO). It was not known whether Z-ISO catalyzes isomerization alone or in combination with other enzymes.

Carotenoids constitute a large class of isoprenoids synthesized by all photosynthetic organisms, some bacteria, fungi and arthropods. Global vitamin A deficiency in children has sparked worldwide efforts to increase the levels of provitamin A carotenoids in food-crop staples. This goal rests on furthering knowledge of how plants control and biosynthesize carotenoids that can be converted in humans to vitamin A. Metabolic engineering and breeding of plants rich in particular carotenoids will continue to be an important objective for addressing the challenges of providing food security in a changing climate. Carotenoid functions are central to plant growth and development. The plant carotenoid-biosynthetic pathway is mediated by enzymes encoded in the nucleus and localized to chloroplasts or other plastids. The carotenoid-biosynthetic reactions begin with formation of the colorless 15-cis-phytoene, which undergoes desaturation and isomerization of double bonds to create carotenoids with yellow, red and orange colors. The pathway requires an electron-transfer chain and plastoquinones to channel electrons and protons produced during desaturation mediated by phytoene desaturase (PDS) and ζ-carotene desaturase (ZDS). PDS produces 9,15,9'-tri-cis-ζ-carotene, which must be isomerized at the 15-15'-cis carbon-carbon double bond to form 9,9'-di-cis-ζ-carotene, the substrate for a second desaturase, ZDS (FIG. 1A). Although light can partially mediate this cis-trans carbon-carbon isomerization, Z—ISO is essential, especially in tissues receiving no light exposure, such as the endosperm tissue, which has been targeted for improvement of provitamin A carotenoids in efforts to alleviate global vitamin A deficiency. Plants with insufficient Z-ISO also grow poorly under the stress of fluctuating temperature. Because climatic variations alter the need for photosynthetic and nonphotosynthetic carotenoids, Z-ISO facilitates plant adaptation to environmental stress, a major factor affecting crop yield. Thus, Z—ISO is essential for maximizing plant fitness in response to environmental changes and for promoting accumulation of provitamin A carotenoids in edible tissues.

Mutants blocked in Z-ISO function accumulate 9,15,9'-tri-cis-ζ-carotene, the putative Z-ISO substrate. When the gene encoding Z-ISO is introduced into *Escherichia coli* cells producing 9,15,9'-tri-cis-ζ-carotene, this carotenoid is isomerized into the putative Z-ISO product, 9,9'-di-cis-ζ-carotene. These data suggest that Z-ISO is required for isomerization of the 15-cis bond in 9,15,9'-tri-cis-ζ-carotene but not the 15-cis bond in 15-cis-phytoene. In *E. coli* experiments, the isomerization activity associated with Z-ISO occurred in the presence of several upstream carotenoid-biosynthetic enzymes needed to produce the Z-ISO substrate. It is therefore desirable to determine whether Z-ISO is a bona fide enzyme that catalyzes isomerization through a unique mechanism requiring a redox-regulated heme cofactor.

The discussion above is merely provided for general background information and is not intended to be used as an aid in determining the scope of the claimed subject matter.

BRIEF DESCRIPTION OF THE INVENTION

A method for isomerizing a double bond is provided. A substrate is exposed to an isomerase enzyme, wherein the isomerase enzyme comprises a redox-regulated ligand switch and heme b cofactor. A reducing agent changes iron (III) to iron (II). The enzyme isomerizes double bonds in the iron (II) state but not in the iron (III) state. In one embodiment, the enzyme is homologous with 15-cis-ζ-carotene isomerase (Z-ISO). An advantage that may be realized in the practice of some disclosed embodiments of the method is that an alternative catalyst is provided that can isomerize double bonds.

In a first embodiment, a method for isomerizing a double bond is provided. The method comprises exposing a substrate to an isomerase enzyme, wherein the isomerase enzyme comprises a redox-regulated ligand switch and heme b cofactor, wherein the heme b cofactor comprises an iron having an iron (III) oxidation state and the substrate comprises a double bond in the substrate with a cis stereochemistry; exposing the isomerase enzyme to a reducing agent such that the isomerase enzyme changes from the iron (III) oxidation state to an iron (II) oxidation state, wherein the isomerase enzyme isomerizes a double bond when in the iron (II) oxidation state and does not isomerize the double bond when in the iron (III) oxidation state; and permitting the double bond in the substrate to undergo isomerization from the cis stereochemistry to a trans stereochemistry, wherein the isomerization is catalyzed by the isomerase enzyme.

In a second embodiment, a method for isomerizing a double bond is provided. The method comprises sequential steps of exposing a carotenoid substrate to an isomerase enzyme, wherein the isomerase enzyme comprises a redox-regulated ligand switch and heme b cofactor, wherein the heme b cofactor comprises an iron having an iron (III) oxidation state and the carotenoid substrate comprises a double bond in the carotenoid substrate with a cis stereochemistry, wherein the isomerase enzyme has fewer than four hundred residues and comprises SEQ ID NO: 11; exposing the isomerase enzyme to a reducing agent in vitro such that the isomerase enzyme changes from the iron (III) oxidation state to an iron (II) oxidation state, wherein the isomerase enzyme isomerizes a double bond when in the iron (II) oxidation state and does not isomerize the double bond when in the iron (III) oxidation state; and permitting a double bond in the carotenoid substrate to undergo isomerization from the cis stereochemistry to a trans stereochemistry, wherein the isomerization is catalyzed by the isomerase enzyme.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 10A is an uncut gel showing heme staining of Z-ISO wherein MBP::Z-ISO was treated with (+TEV) and without (−TEV) TEV protease;

FIG. 10B is an uncut gel showing Coomassie staining of Z-ISO wherein MBP::Z-ISO was treated with (+TEV) and without (−TEV) TEV protease;

expressed in *E. coli* cells harboring the pACCRT-EBP vector which confers accumulation of the Z-ISO substrate. The control sample is from cells containing the pACCRT-EBP vector alone. Upper panel: Western blot analysis using anti Z-ISO. Lower panel: Coomassie stain for protein samples used for immunodetection. One lane in both panels was blocked because the sample was unrelated to the current disclosure; and FIG. 15 depicts maize Z-ISO codon optimized for *E. coli* wherein the top panel shows DNA sequence Sac I/Bam H1 sites (upper case) added at 5' and 3' ends for cloning into pUC57 and the Z-ISO start code is underlined; the bottom panel shows the protein sequence with the predicted transit sequence underlined.

DETAILED DESCRIPTION OF THE INVENTION

Figure 2A:
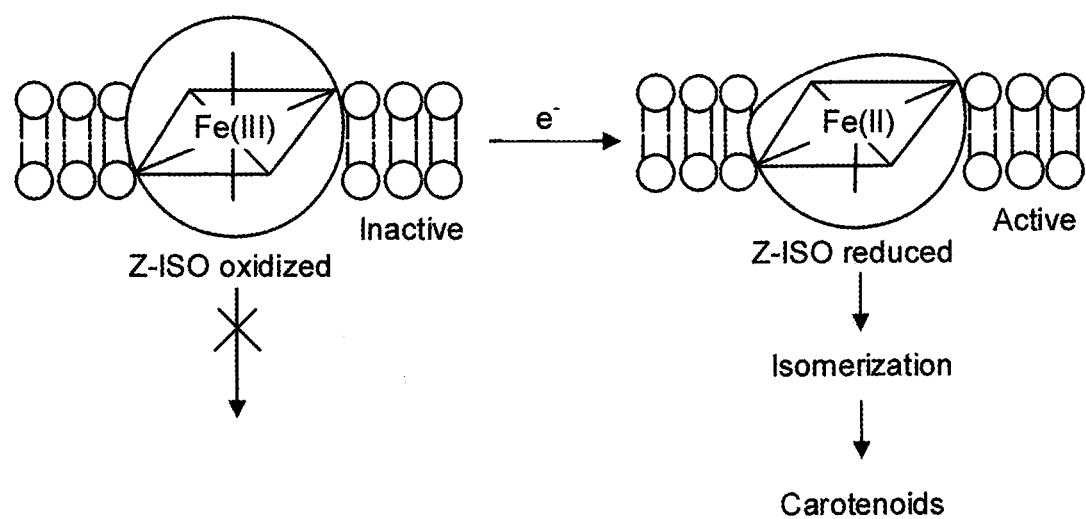
FIG. 2A is a schematic depiction of Z-ISO in an oxidized (inactive) state and in a reduced (active) state.

Without wishing to be bound to any particular theory, carotenoid isomerization of the central double bond is believed to involve 15-cis-ζ-carotene isomerase (Z-ISO) with an unusual heme-dependent chemistry. See FIG. 2A. Z-ISO has been identified as a bona fide enzyme and integral membrane protein. Z—ISO independently catalyzes the cis-trans isomerization of the 15-15' carbon-carbon double bond in 9,15,9'-cis-ζ-carotene to produce the substrate required by the subsequent biosynthetic-pathway enzyme. This isomerization depends upon a ferrous heme b cofactor that undergoes redox-regulated ligand switching between the heme iron and alternate Z-ISO amino acid residues. Heme b-dependent isomerization of a large hydrophobic compound in a membrane was previously undescribed. As an isomerase, Z—ISO represents a new prototype for heme b proteins and potentially uses a new chemical mechanism.

Two isoforms of Z-ISO are provided in SEQ ID NO:9 and SEQ ID NO: 10. SEQ ID NO: 10 is the same as SEQ ID NO: 9 except in that residues 257-285 are different and residues 286-367 are omitted. Both isoforms share a common sequence given by SEQ ID NO: 11. In one embodiment, an isomerase enzyme is used than has fewer than four hundred residues and comprises the common sequence given by SEQ ID NO: 11. In another embodiment, the isomerase enzyme is SEQ ID NO: 9 or SEQ ID NO: 10. In another embodiment, the isomerase enzyme is homologous with (e.g. at least 70% homologous, 80% homologous, 90% homologous or 95% homologous) either SEQ ID NO: 9 or SEQ ID NO: 10.

Z-ISO and its related protein sequences, including the NnrU protein, contain a redox-regulated ligand switch and heme b cofactor which can be used to control the cis to trans isomerization of C=C and other double bonds, including N=O, and for control of carotenoid biosynthesis flux and carotenoid levels through Z-ISO heme redox state and through manipulation of internal ligands and external ligands, including binding of substrates and diatomic gasses to the heme iron. The enzyme is in an inactive state when the iron is in a +3 oxidation state. The enzyme is in an active state when the iron is in a +2 oxidation state. The activity of the enzyme can therefore be controlled by controlling the redox conditions of the enzyme environment.

This disclosure provides knowledge of the Z-ISO mechanism that will now allow for post-translational control of the biosynthesis of carotenoids, as well as the control of the cis to trans isomerization of double bonds contained by other synthetic (non-native) substrates.

In other embodiments, by modifying the Z-ISO (and other related sequences including NnrU) protein sequence from any organism, including modification of the heme ligand residues, will result in creation of new enzymes that recognize novel substrates on which Z-ISO can catalyze the cis to trans isomerization of double bonds to form compounds with novel chemical properties. After benefiting from reading this specification, those skilled in the art will appreciate such new enzymes can be generated for specific substrates using conventional biotechnology techniques including, for example, mutagenesis.

Figure 1A:
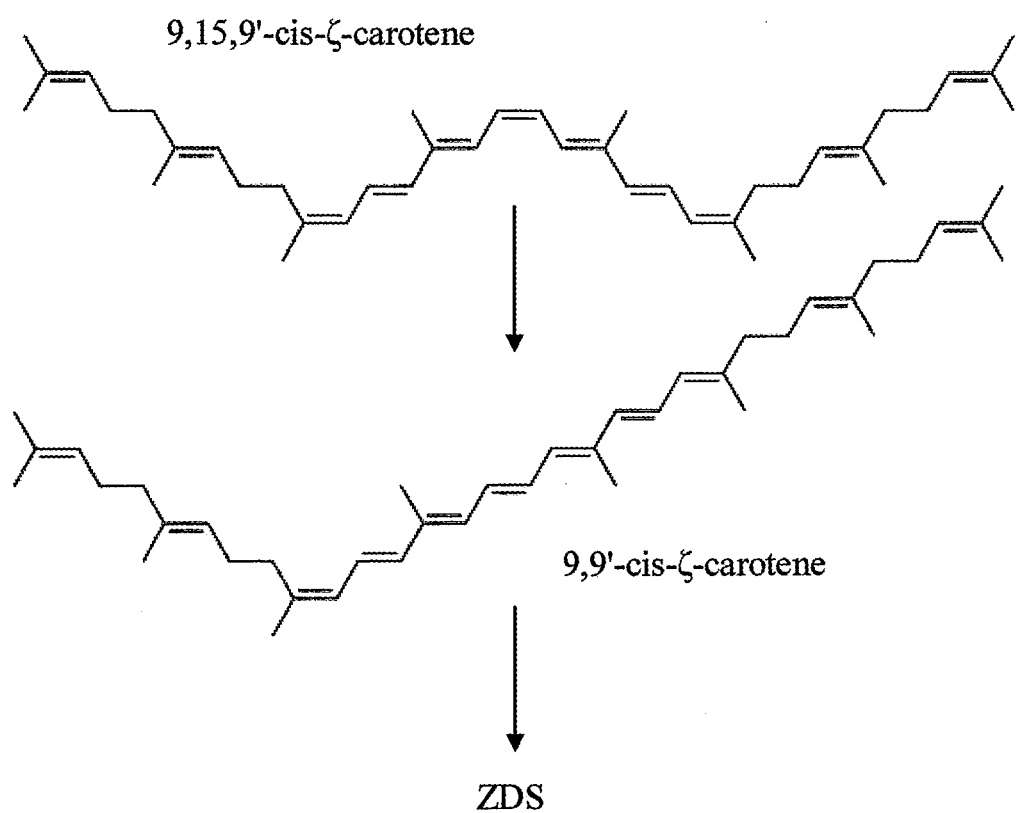
FIG. 1A depicts a cis-trans isomerization of 15-cis-ζ-carotene isomerase (Z-ISO) to trans Z-ISO.
Figure 1B:
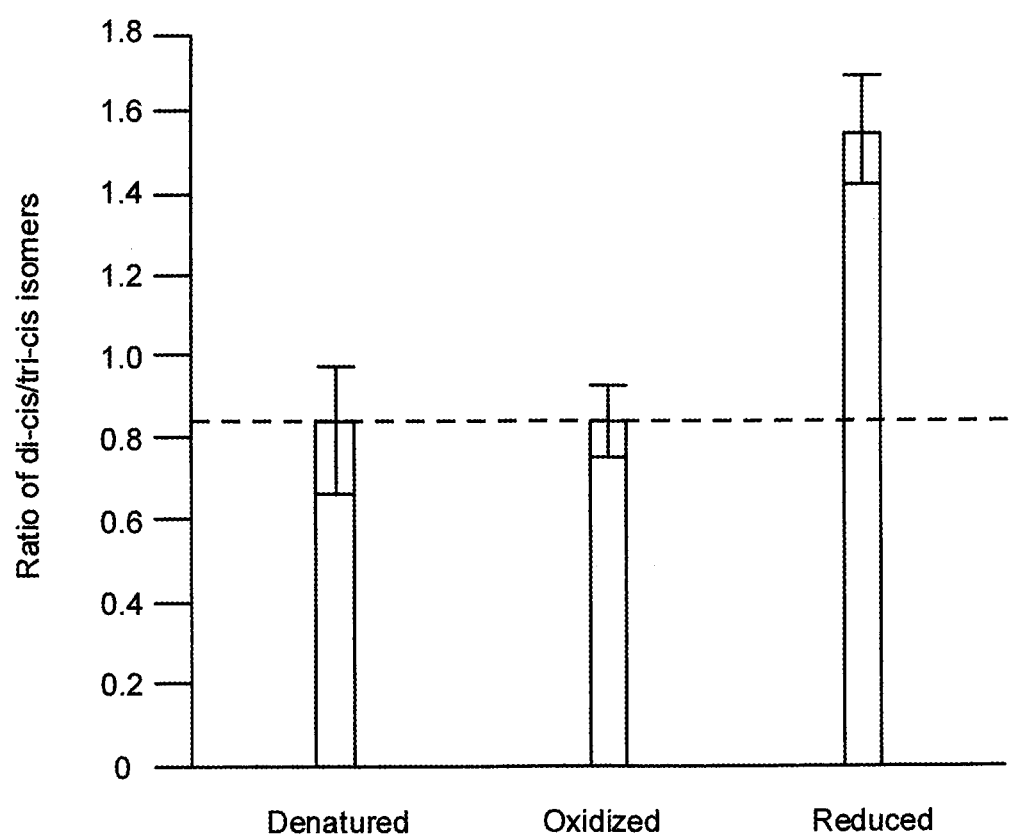
FIG. 1B is graph depicting the conversion of cis Z-ISO to trans Z-ISO is only catalyzed in the presence of a reduced enzyme complex.
Figure 7A:
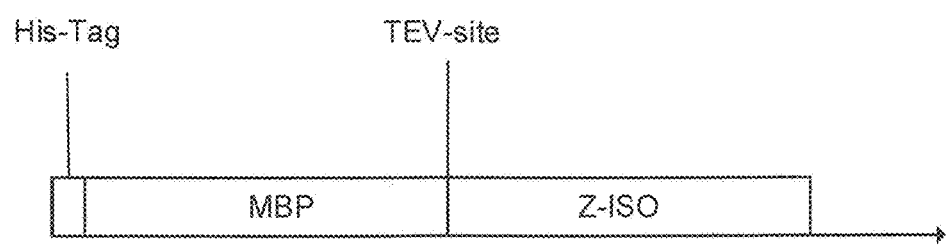
FIG. 7A is a cartoon showing Z-iso fusion protein containing histidine tag (His-Tag), maltose binding protein (MBP), TEV protease cleavage site and Z-ISO.
Figure 7B:
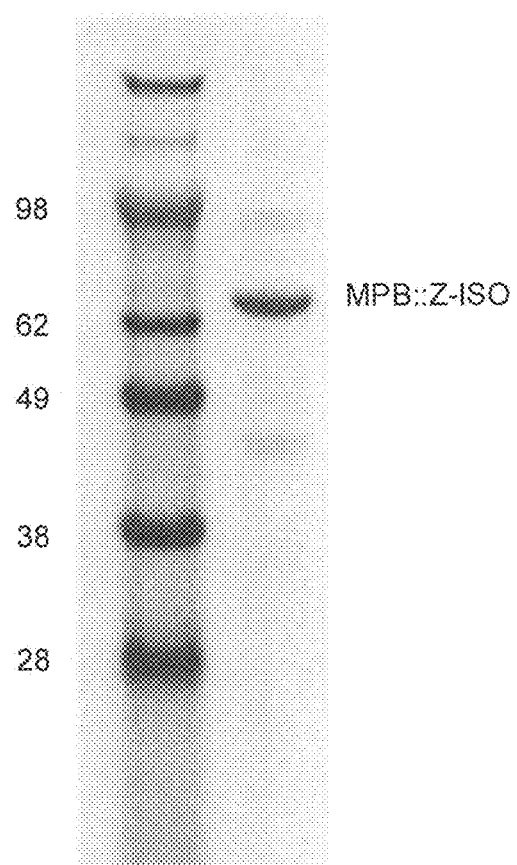
FIG. 7B is an image of a gel showing Z-ISO fusion protein of 90% purity analyzed by SDS-PAGE wherein MBP::Z-ISO (marked by narrow) was used for the in vitro assay (after cleavage) and for all subsequent spectroscopic analyses with molecular weight makers (kD) shown in left lane.

To directly test whether Z-ISO is a bona fide enzyme an in vitro assay was developed with isolated Z-ISO from *Zea mays* (SEQ ID NO: 12) and artificial liposomes containing the Z-ISO substrate. First, the substrate from *E. coli* was purified and combined with lipids to form artificial liposomes. Next, Z-ISO was overexpressed and purified as a TEV protease-cleavable maltose-binding protein (MBP) fusion (MBP::Z-ISO). See FIG. 7A and FIG. 7B. Last, the isolated fusion protein of 90% purity (FIG. 7B) was incubated with TEV protease to cleave Z-ISO away from the fused MBP before initiation of the isomerization reaction. Conversion of the substrate to product occurred only in the presence of Z-ISO that had been pretreated with dithionite to a final concentration of 10 mM to create reducing conditions (FIG. 1B). The as-purified enzyme (considered to be oxidized), as well as heat-denatured Z-ISO, was not functional. The Z-ISO catalyzed isomerization only when the reaction was conducted under reducing conditions but not oxidizing conditions. In this experiment, the liposomes used for the in vitro assay were also essential, because reactions lacking liposomes also did not work.

To gain insight into the mechanism of isomerization catalytic motifs or other characteristic domains in Z-ISO were identified. BLAST analysis suggested that, although Z-ISO is highly conserved in plants, it shares sequence homology (about 76% similarity) with only NnrU, an uncharacterized membrane protein associated with nitric oxide (NO) metabolism in noncarotenogenic bacteria that perform denitrification. In addition, a chloroplast-targeting sequence was previously identified in Z-ISO, thus suggesting that Z-ISO is a plastid-localized protein. Bioinformatic approaches were used to generate hypotheses on the location and function of Z-ISO and tested them further.

MEMSAT3 predicted seven transmembrane (TM) domains in maize Z-ISO, with TM2-TM7 showing homology to the corresponding TM domains in NnrU. In contrast to a functional *Arabidopsis* transcript (ZISOJ1.1), a shorter *Arabidopsis* transcript (ZISO1.2) encodes a nonfunctional protein with one less TM domain at the C terminus. The effect of the deletion suggests that the C-terminal M domain is important for the function (for example, activity or proper folding) of Z-ISO.

Figure 8A:
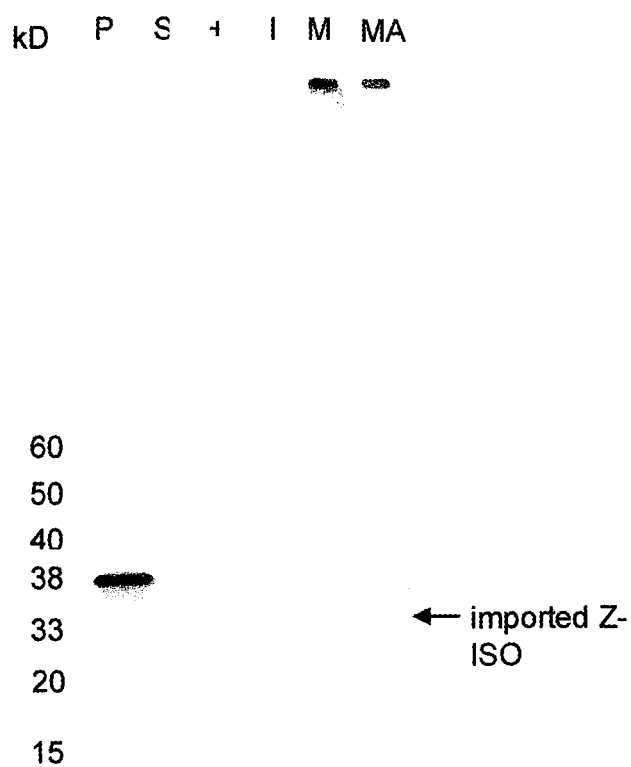
FIG. 8A shows a gel of in vitro import into pea chloropleases wherein 38 kD Z-ISO is cleaved upon import to 33 kD, suggesting a 5 kD transit peptide. After import, chloroplasts were treated with thermolysin (+) to remove non-specifically bound protein. Chlorplasts were also fractionated into soluble (S) and membrane (M) fractions; an equal amount of the membrane fraction as in M was alkaline-treated (MA) to remove peripheral membrane proteins.
Figure 8B:
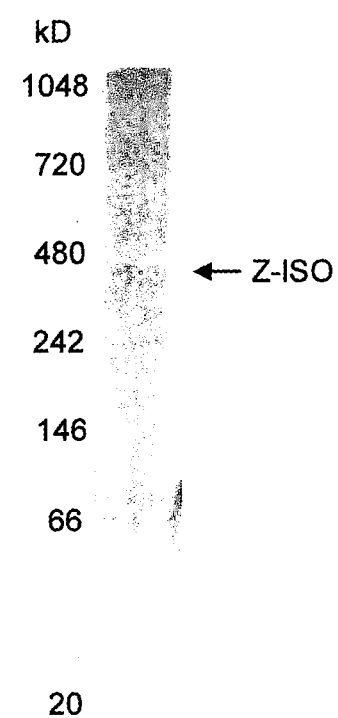
FIG. 8B shows Z-ISO is in a ~480 kD complex in chloroplasts as separated on a Blue Native gel.

To test the prediction that Z-ISO is targeted to the chloroplast, the gene encoding GFP was fused downstream of the gene encoding Z-ISO, including its transit peptide. The fusion construct was transiently expressed in maize leaf protoplasts. GFP fluorescence confirmed that Z-ISO colocalized in the chloroplasts together with chlorophyll). In vitro chloroplast protein import demonstrated that Z-ISO is a chloroplast integral membrane protein (FIG. 8A), as predicted by the topology predictions. When taken together, these observations suggest that Z-ISO is localized in chloroplast membranes. Z-ISO was also found to exist in a high-molecular-weight protein complex of about 480 kDa (FIG. 8B), as similarly noted for other carotenoid enzymes.

Next, homology-modeling tools were applied to look for structural homologies missed by the BLAST analysis. Homology modeling was expected to be limited by the underrepresentation of membrane-protein structures in the Protein Data Bank, owing to the inherent difficulties in crystallizing membrane proteins. Homology modeling of Z-ISO with the Meta Server program modeled the residues of Z-ISO onto an integral membrane protein, the diheme cytochrome b subunit of quinol-fumarate oxidoreductase. The fold-recognition program LOOPP predicted that Z-ISO might contain nonheme iron. These programs are based on unique algorithms, and therefore the templates chosen for modeling by the programs were different. However, neither NnrU nor Z-ISO had been annotated as metalloproteins.

Figure 9A:
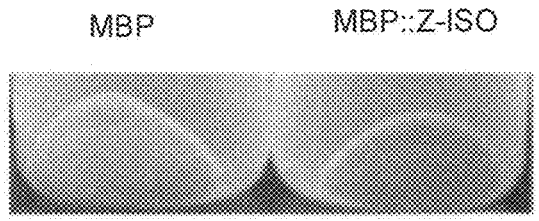
FIG. 9A are images of cell pellets expressing MBP::Z-ISO that were brown colored compared with pellets expressing MBP only.
Figure 9B:
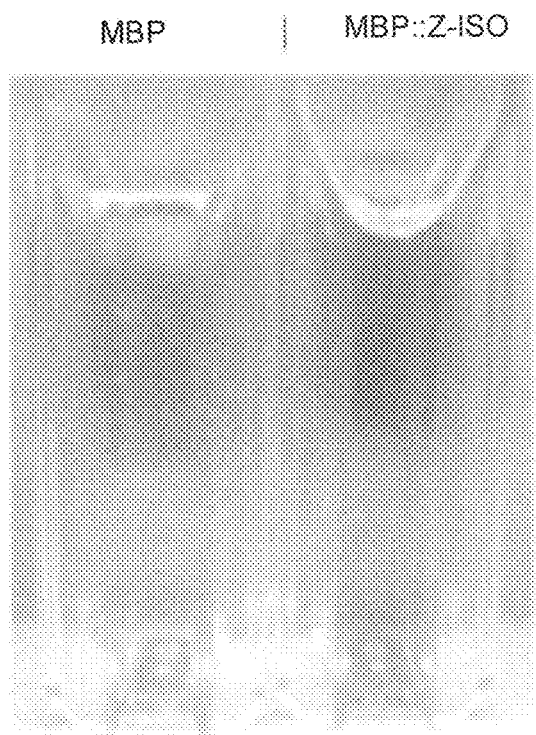
FIG. 9B are images of MBP::Z-ISO protein extracts that were brown suggesting presence of a cofactor compared with pellets expressing MBP only.

To test the prediction that Z-ISO is a metalloenzyme, inductively coupled plasma optical emission spectrometry (ICP-OES) was used to measure the metal content. The result showed that iron, but not calcium, copper, nickel, magnesium, manganese, molybdenum or zinc, is present in the MBP::Z-ISO fusion. Because MBP is not a metallo-protein, the protein-bound iron was postulated to be exclusively associated with Z-ISO. Cultures with MBP::Z-ISO are brown (FIG. 9A), as is the purified protein (FIG. 9B), consistent with the presence of heme or nonheme iron.

Figure 2B:
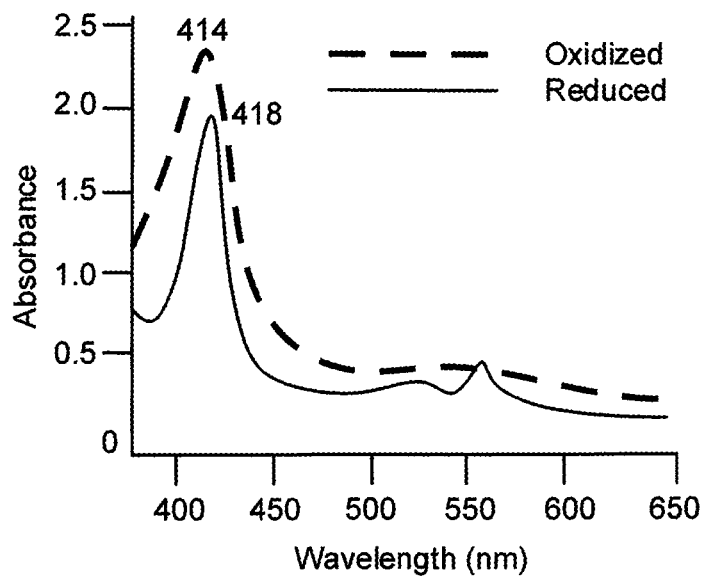
FIG. 2B is a UV-vis absorption spectrum from a pyridine hemochrome assay of nickel affinity-purified MBP::Z-ISO protein extract.
Figure 2C:
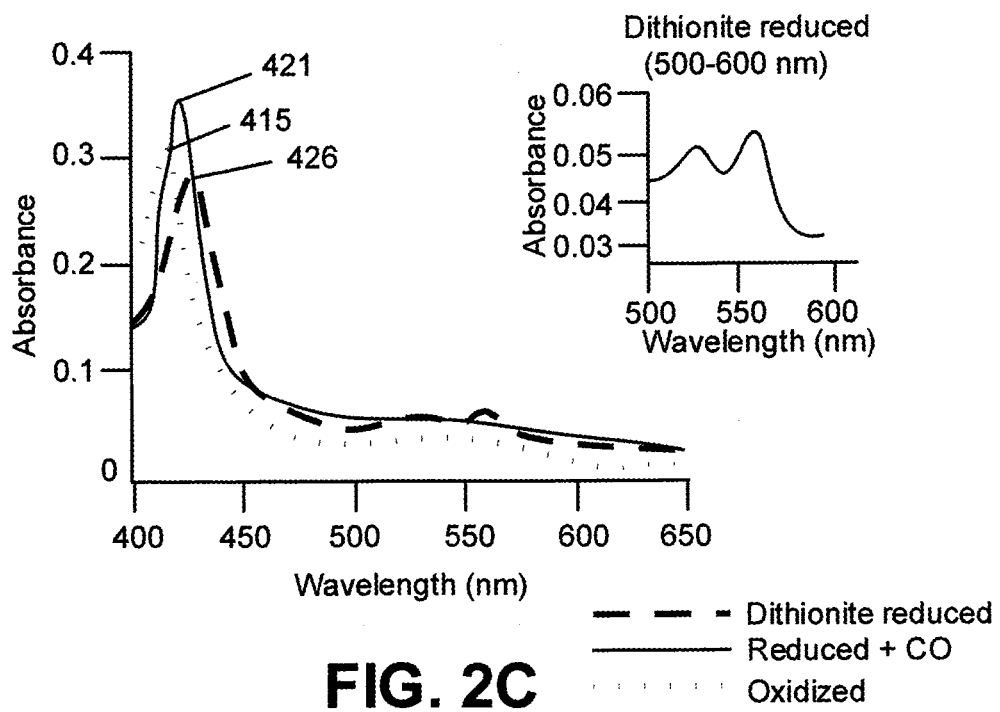
FIG. 2C is a UV-vis absorption spectrum from MBP::Z-ISO in isolated (oxidized), dithionite reduced or dithionite reduced and CO treated states.
Figure 2D:
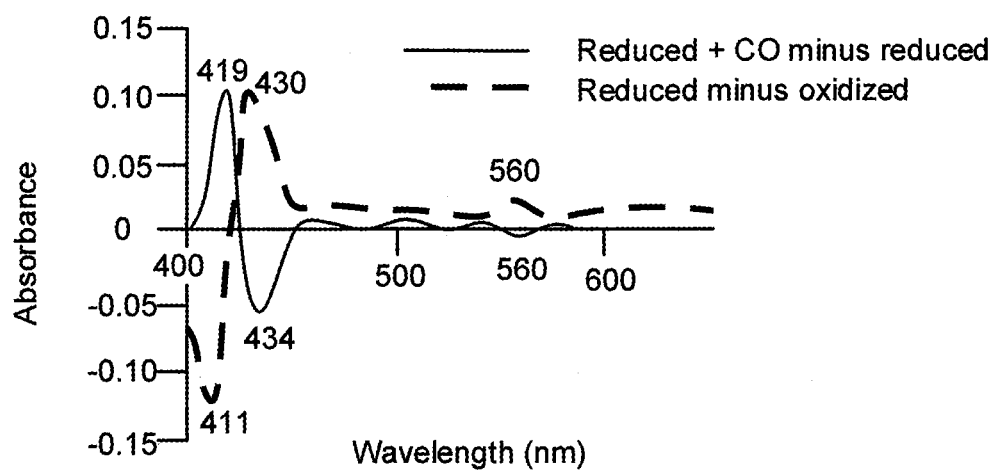
FIG. 2D is a difference spectrum of data from FIG. 2C.
Figure 11:
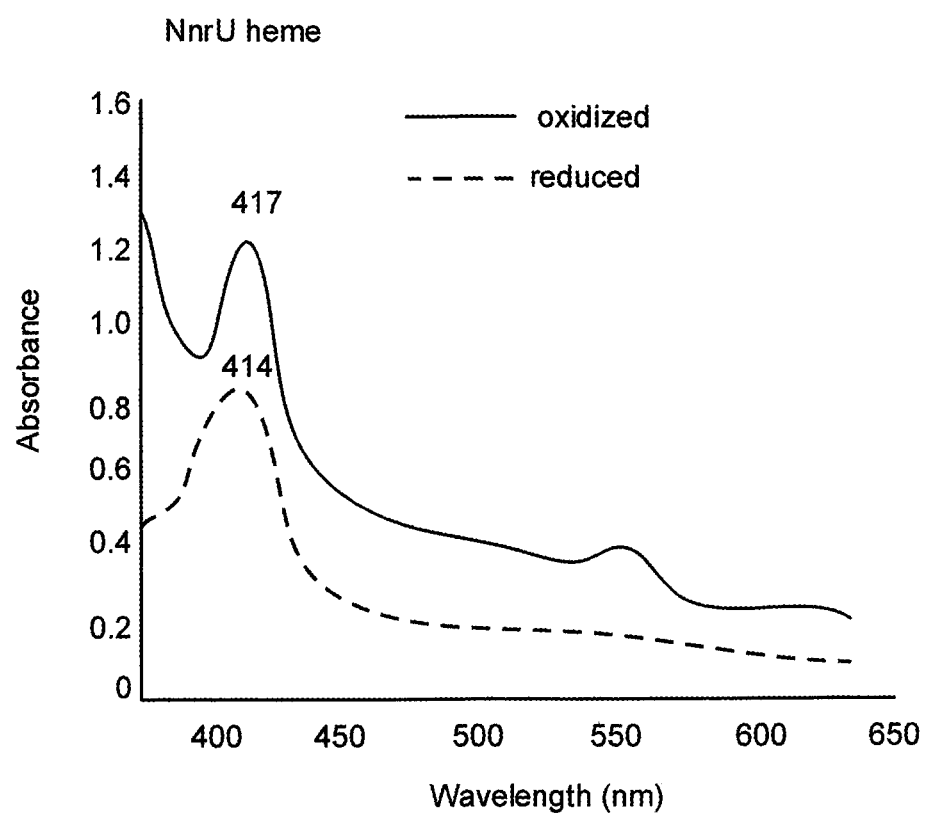
FIG. 11 is a graph showing NnrU (Agrobacterium tumefaciens C58) expressed as a fusion protein in E. coli, purified, and treated with and without dithionite by depicting a pyridine hemochrome assay of the extracts analyzed by UV-visible absorption spectroscopy.

To test specifically for heme, MBP::Z-ISO was separated and Z—ISO and MBP were cleaved by SDS-PAGE and stained for heme and then for total protein. The results showed that both MBP::Z-ISO and Z-ISO contained heme, whereas MBP did not (FIG. 10A and FIG. 10B). A pyridine hemochrome assay was conducted (FIG. 2B) to examine the heme cofactor independent of Z-ISO and found that it is a heme b, on the basis of spectroscopic signature. The related NnrU protein is also known to contain a heme b (FIG. 11). UV-visible (UV-vis) absorption spectroscopy of as-purified Z-ISO together with its bound heme indicated the presence of an oxidized, ferric (Fe(III) state) heme. To generate the spectrum of the reduced Z-ISO heme (with a ferrous (Fe(II)) heme iron, the as-purified Z-ISO was treated with dithionite. The spectrum of the dithionite-reduced Z-ISO (FIG. 2C) is similar to spectra of cytochromes containing heme b with two axial histidine ligands. Carbon monoxide (CO) was used as a diagnostic probe to test whether the heme could coordinate electrons with an exogenous ligand. The shift in the UV-vis spectrum attributed to the heme indicated that CO could bind and coordinate to the heme iron of Z-ISO (FIG. 2C and FIG. 2D). The binding was stoichiometric, given that the absorbance associated with CO binding was almost equivalent to that associated with the reduced heme. That is, the absorbance of the α-band trough at 560 nm in the CO difference spectrum (FIG. 2D) was about 90% the intensity of the α-band peak for the same sample in the reduced minus oxidized spectrum. The comparison indicated that at least 90% of the reduced heme had bound CO. This result suggests that one of the axial amino acid ligands may be displaced by an exogenous ligand. The import of this observation is that the Z-ISO heme iron may not be limited to shuttling electrons, as in the case of hemes that participate in electron transfer, but instead the Z-ISO heme iron may have a role in catalysis.

Figure 2E:
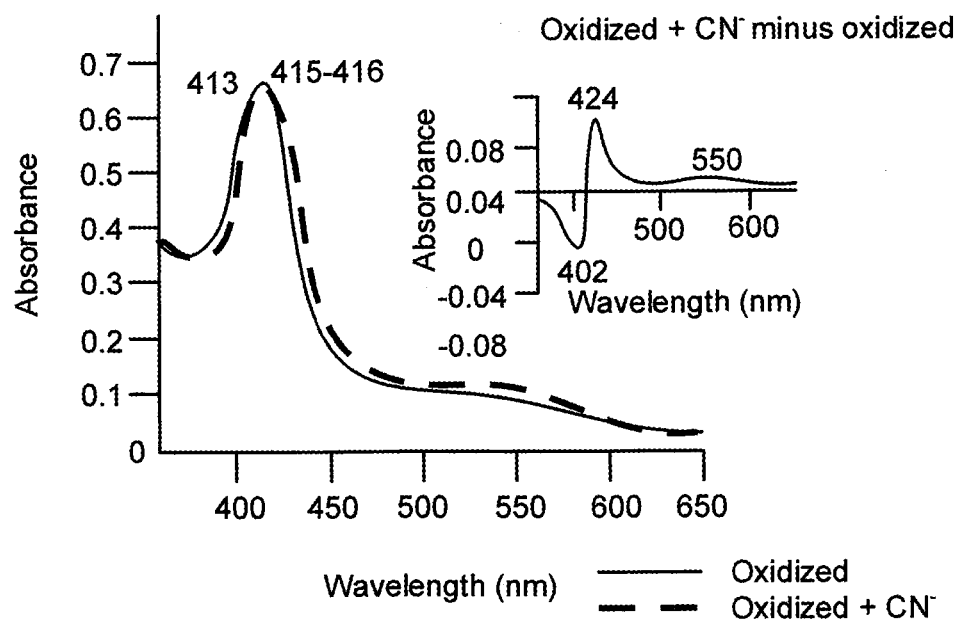
FIG. 2E is a UV-vis absorption spectrum showing binding of cyanide (2 mM) to as-purified Z-ISO (21 μM) wherein the inset is the difference spectra comparing cyanide binding to dithionite-reduced enzyme)
Figure 12:
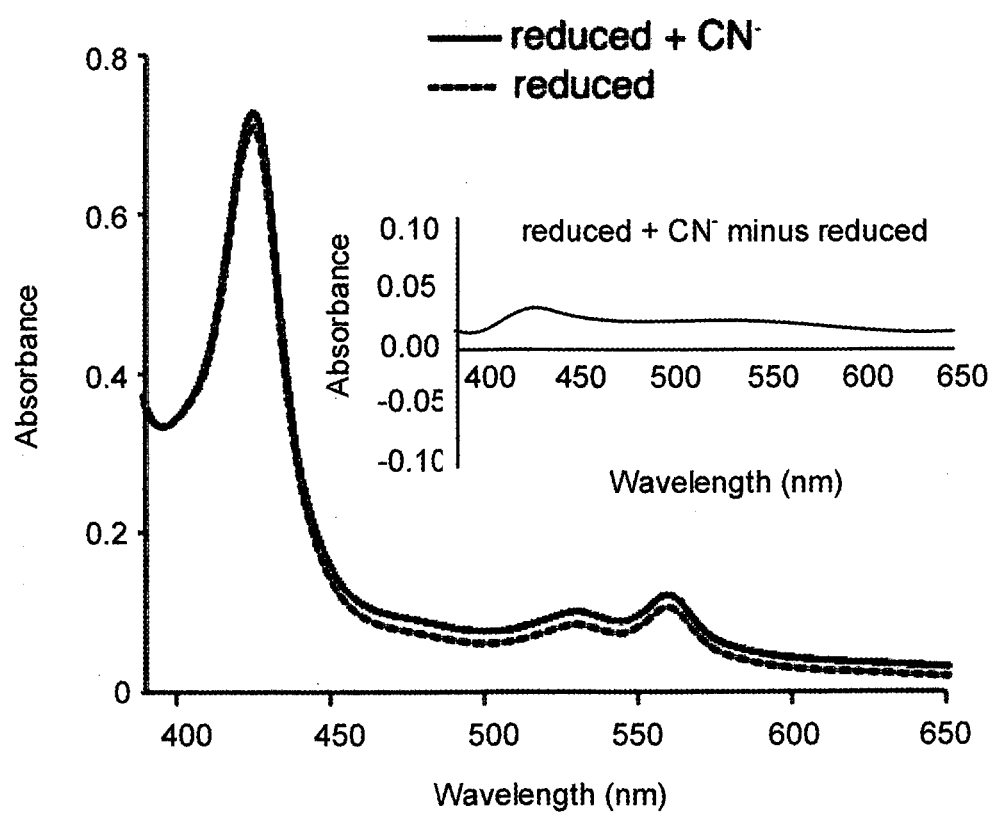
FIG. 12 is a graph showing CN-binding to ferrous Z-ISO wherein MBP::Z-ISO, 75.46 kDa (1.58 mg/mL, 21 μM) treated with dithionite, was incubated with KCN at a final concentration of 2 mM. UV visible spectra were recorded before and immediately after addition of KCN. The inset shows the difference spectrum.

UV-vis absorption spectroscopy analysis showed that an exogenous ligand can bind to the heme iron in the Fe(II) state, but it was not known whether an exogenous ligand could displace an axial ligand if the heme were in the Fe(III) state. To test this possibility cyanide ($CN^-$), which is known to bind preferentially to ferric rather than ferrous heme, was introduced. Cyanide was added to both the as-purified enzyme with oxidized, Fe(III) heme and to the dithionite-reduced enzyme carrying a reduced, Fe(II) heme and the UV-vis absorption was measured. See FIG. 2E. Binding of cyanide to the Fe(III) heme of Z-ISO was observed under saturating concentrations of KCN, as indicated by the shift in the Soret peak (from 413 nm to 415 nm or 416 nm), and the new spectrum resembled that of cyanomyoglobin, which has histidine as the protein-anchoring, or so-called proximal, ligand. However, binding of cyanide to the ferric iron was substoichiometric, on the basis of analysis of the difference spectra. Addition of cyanide- to the ferrous enzyme showed no spectral change (FIG. 12). These results support the presence of a pentacoordinate, high-spin monohistidine ligand-bound ferric heme (in equilibrium with low-spin hexacoordinate heme), which can bind exogenous ligand in the oxidized, inactive enzyme. The substoichiometric binding of cyanide suggests that this pentacoordinate, high-spin species represents a small subset of the total ferric heme.

Figure 3A:
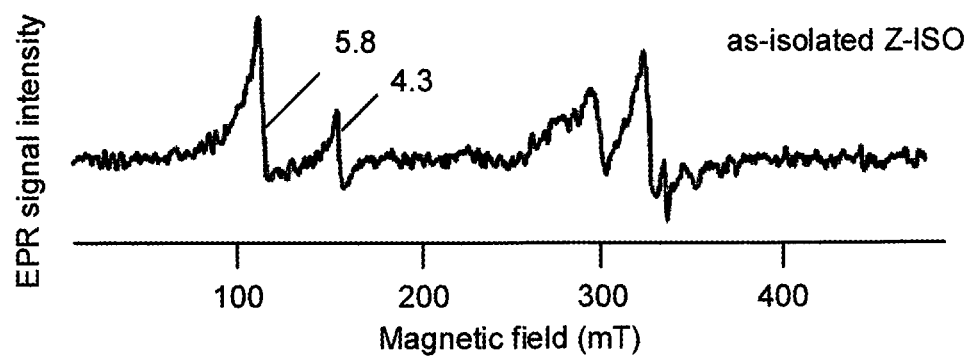
FIG. 3A is an EPR spectrum of as-purified Z-ISO.
Figure 3B:
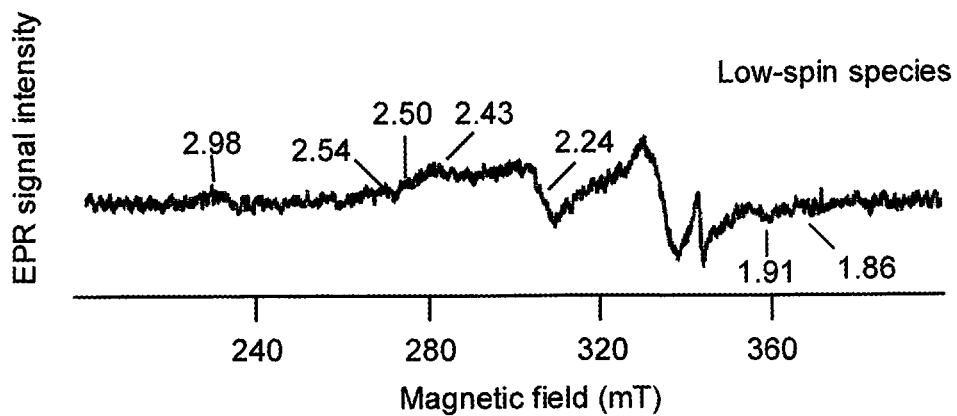
FIG. 3B is an EPR spectrum showing an enlarged view of the low-spin region of FIG. 3A.

An X-band EPR spectrum of the as-purified MBP::Z-ISO fusion protein indicated the presence of a high-spin ferric heme (i.e., heme b with an axial histidine ligand) at a proportionality factor (g):of 5.8 and of multiple low-spin hemes with broad EPR signals (FIG. 3A and FIG. 3B and Table 1).

TABLE 1

EPR parameters for the iron species present in as-purified Z-ISO

| Iron Species | Ligands | g factors |
| --- | --- | --- |
| High-spin heme | His | 5.8, 2.0 |
| Low-spin heme #1 | bis-His | 2.98, 2.24$^a$, 1.42 |
| Low-spin heme #2 | His-Cys | 2.54, 2.24$^a$, 1.86 |
| Low-spin heme #3 | His-Cys | 2.50, 2.23$^a$, 1.86 |
| Low-spin heme #4 | His-Cys | 2.43, 2.24$^a$, 1.92 |
| Nonheme iron$^b$ | N/D | 4.3 |

$^a$Multiple sets of overlapping signals
$^b$A minor species likely derived from non-specific iron binding
N/D: not determined In addition, a minor nonheme-iron species was observed at g of 4.3, which was postulated to be nonspecifically bound to Z-ISO. The low-spin heme EPR signals (shown in FIG. 3A and FIG. 3B) are consistent with the existence of two major types of low-spin heme species with either a bis-histidine or histidine-cysteine axial ligand set, respectively.

TABLE 2

Conserved residues mutagenized to Alanine (A) and tested for activity by functional complementation in E. coli.

| Mutagenesis of conserved residue to alanine (A) | Whether required for Z-ISO function |
| --- | --- |
| H150 mutated to A | Yes |
| H191 mutated to A | No |
| H208 mutated to A | No |
| H241 mutated to A | No |
| H253 mutated to A | No |
| C263 mutated to A | No |
| H266 mutated to A | Yes |
| D294 mutated to A | Yes |

There is an interest is producing certain carotenoids. In one embodiment, the activity of the isomerase is intentionally blocked by genetically modifying a plant to prevent the plant's ability to form the functional heme-based cis-trans isomerase. In such genetically modified plants, the biosynthesis of un-isomerized carotenoids is enhanced. For example, the plant may be genetically modified to block Z-ISO function by entirely removing a gene that encodes for Z-ISO (i.e. a gene that encodes for SEQ ID NO. 12). Alternatively, the plant may be genetically modified to block Z-ISO function by mutating the DNA of the plant such that the resulting isomerase has a mutation including one or more of H150, H266 or D294. Such plants might include tomato, apples, citrus, potatoes.

The low-spin species at g of 2.98 is assigned as a hexacoordinate heme with a bis-histidine axial ligand set, on the basis of the similarity of its g factors to those of other heme species with a bis-imidazole axial ligand set. The signals at g of 2.54, 2.50 and 2.43 are attributed to the $g_x$ tensors for multiple components of a hexacoordinate low-spin heme species with a histidine-cysteine axial ligand set. Such low-spin species typically display a narrow distribution of the g factors, owing to pronounced delocalization of the spin density to the cysteine ligand. The heterogeneity of this histidine-cysteine-coordinated heme species probably originated from variations in the coordination position as well as the protonation or hydrogen-bonding state of the cysteine ligand. Previous studies on other systems have demonstrated that the g factors for histidine-cysteine-coordinated heme species are sensitive to the electronic properties of the heme environment and the protonation state of the axial ligands. Next, the as-purified sample was chemically reduced with dithionite and the reduced sample was EPR silent. With addition of NO, a strong EPR signal at the g=2 region was detected, which was attributed to the formation of a low-spin hexacoordinate Fe(II)-nitrosyl heme complex. NO binding is consistent with the finding that reduced MBP::Z-ISO also binds CO (FIG. 2C and FIG. 2D). The EPR spectrum of the Fe(II)-nitrosyl complex of MBP::Z-ISO is similar to spectra of other Fe(II)-nitrosyl adducts of histidine-ligated hemes, such as those reported in cytochrome c oxidase, cytochrome c peroxidase, heme oxygenase, hemoglobin, myoglobin and horseradish peroxidase, thus suggesting that a histidine residue is retained as the axial ligand of the ferrous heme with NO is bound.

EPR analysis revealed high-spin and low-spin hemes. A high-spin heme can have an easily observable EPR signal, even if it is a minor component. To further examine the hemes in the same sample as used for EPR, magnetic circular dichroism (MCD) was used, which detects mainly the heme chromophore (300-700 nm). To ascertain a detection limit of the percentage of high-spin heme in a sample containing a mixture of low-spin and high-spin heme, the MCD and UV-vis absorption spectra of Fe(III) cytochrome b5 (100% low-spin species) was compared to Fe(III) Mb (met-aqua-Mb):(about 100% high spin) in a series of low-spin/high-spin mixtures (95:5, 90:10, 80:20 and 50:50). This comparison showed that Fe(III) Z-ISO (FIG. 4A) contains less than 20% (probably less than 10%) high-spin heme at ambient temperature, presumably from equilibrium dissociation of an axial ligand from the low-spin heme.

Figure 4A:
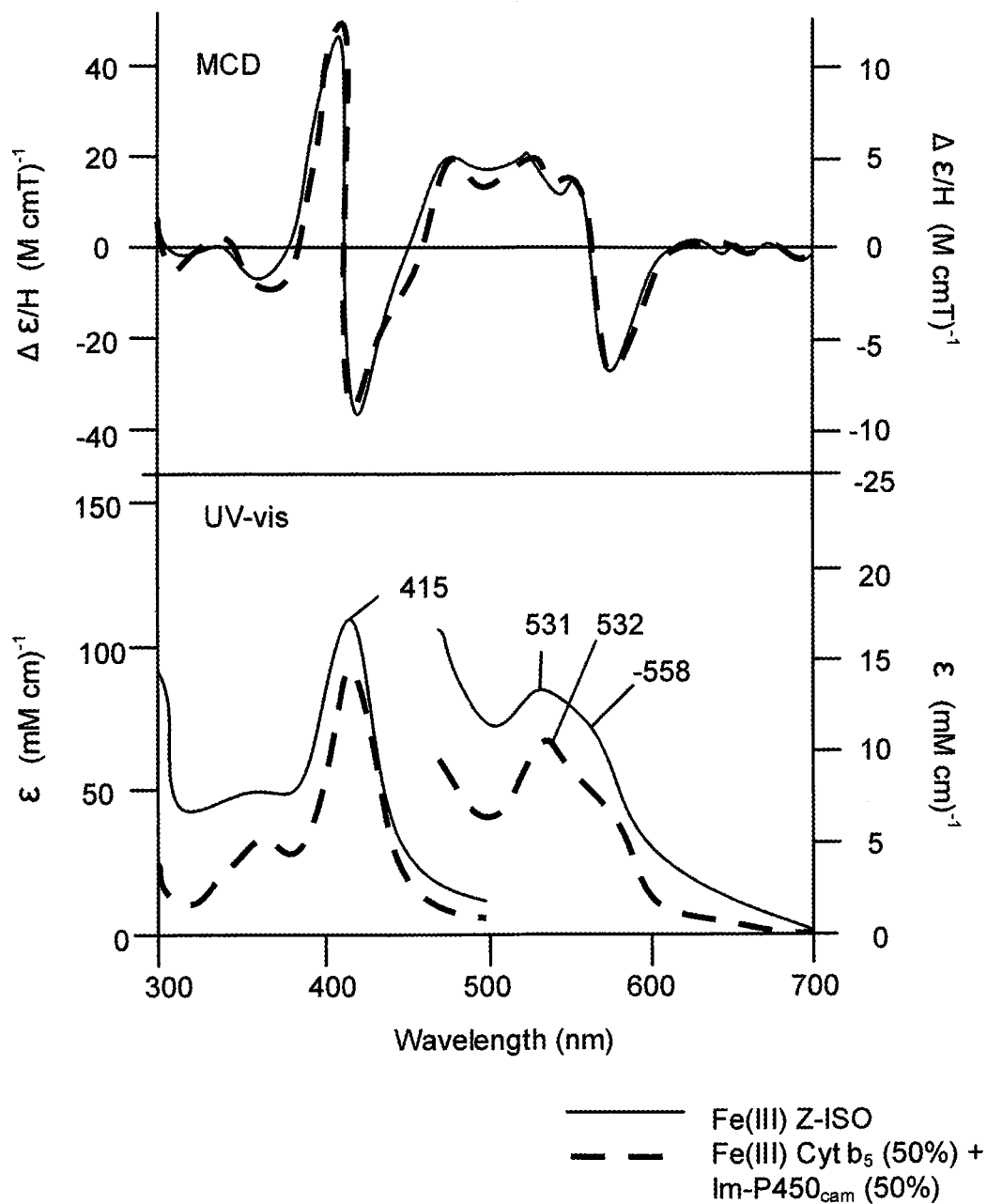
FIG. 4A depicts MCD and UV-vis spectra of as-purified Fe(III) Z-ISO (oxidized) compared with spectra of a 50-50 mixture of Fe(III) cytochrome (cyt)$b_5$ (bis-histidine) and imidazole (Im)-bound Fe(III) P450$_{cam}$ (histidine-cysteine)
Figure 4B:
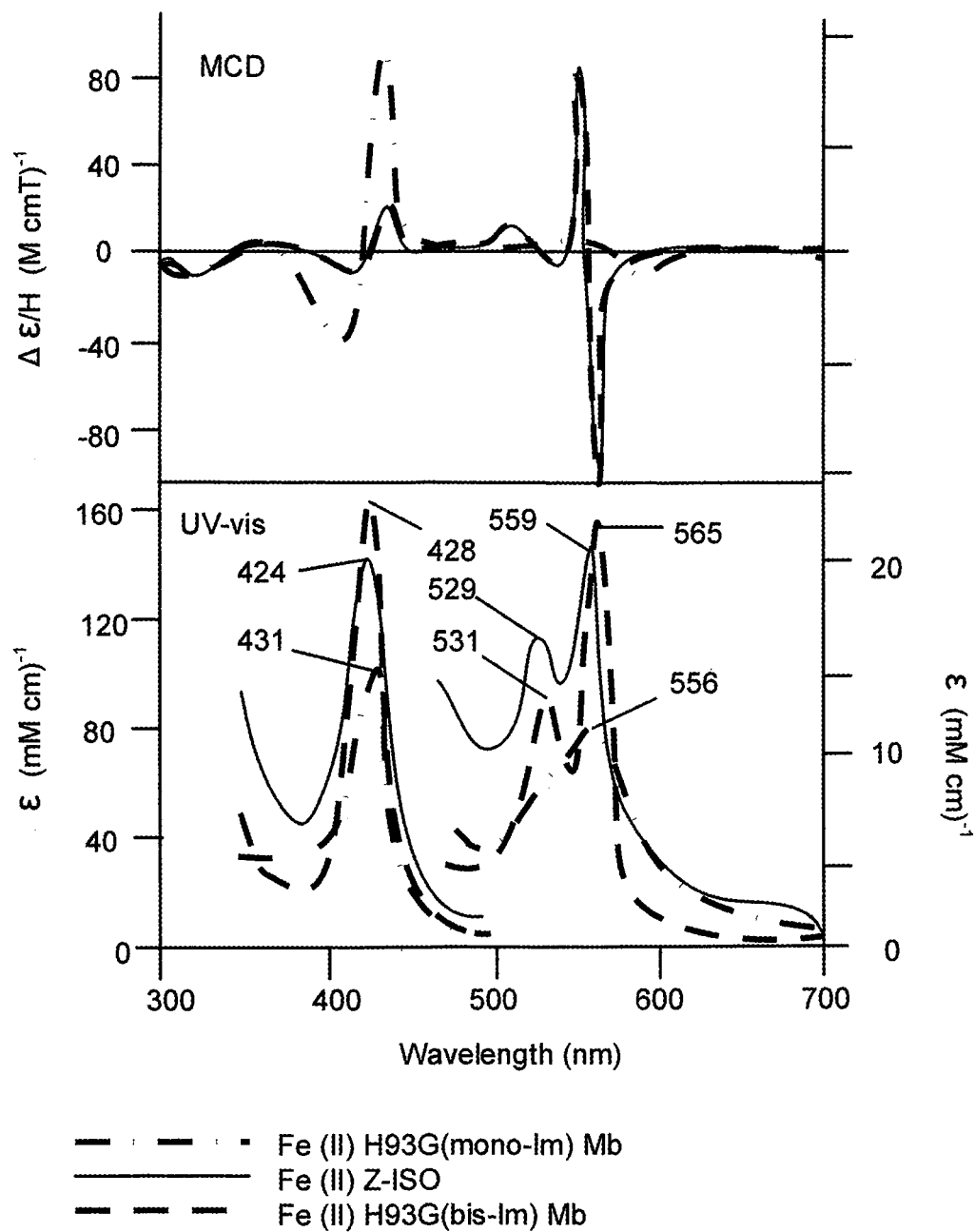
FIG. 4B depicts MCD and UV-vis spectra of as-dithionite-reduced ferrous (Fe(II)) Z-ISO compared with spectra of mono and bis Im-bound H93G Mb.

MCD also showed that ferric Z-ISO has two ligand pairs (histidine-histidine and histidine-cysteine), consistent with the EPR results. This was determined by comparing the as-purified Z-ISO spectrum with that of a simulated mixture of cytochrome b5 (bis-histidine) and imidazole (Im)-bound P450$_{cam}$ (histidine-cysteine) (FIG. 4A). The data show a good fit to two ligand-coordination modes in low-spin ferric Z-ISO at about a 1:1 ratio. If there is only one heme center in the protein, histidine and cysteine might occupy the distal side of the heme as alternative ligands while the proximal side is ligated by a common histidine. The MCD spectrum of the dithionite-reduced Z-ISO. MCD showed a single heme species in the reduced Z-ISO coordinated by bis-histidine (FIG. 4B). Importantly, the amount of reduced histidine-histidine heme was equivalent to the combined concentration of the histidine-histidine and histidine-cysteine heme seen in oxidized Z-ISO.

Figure 5A:
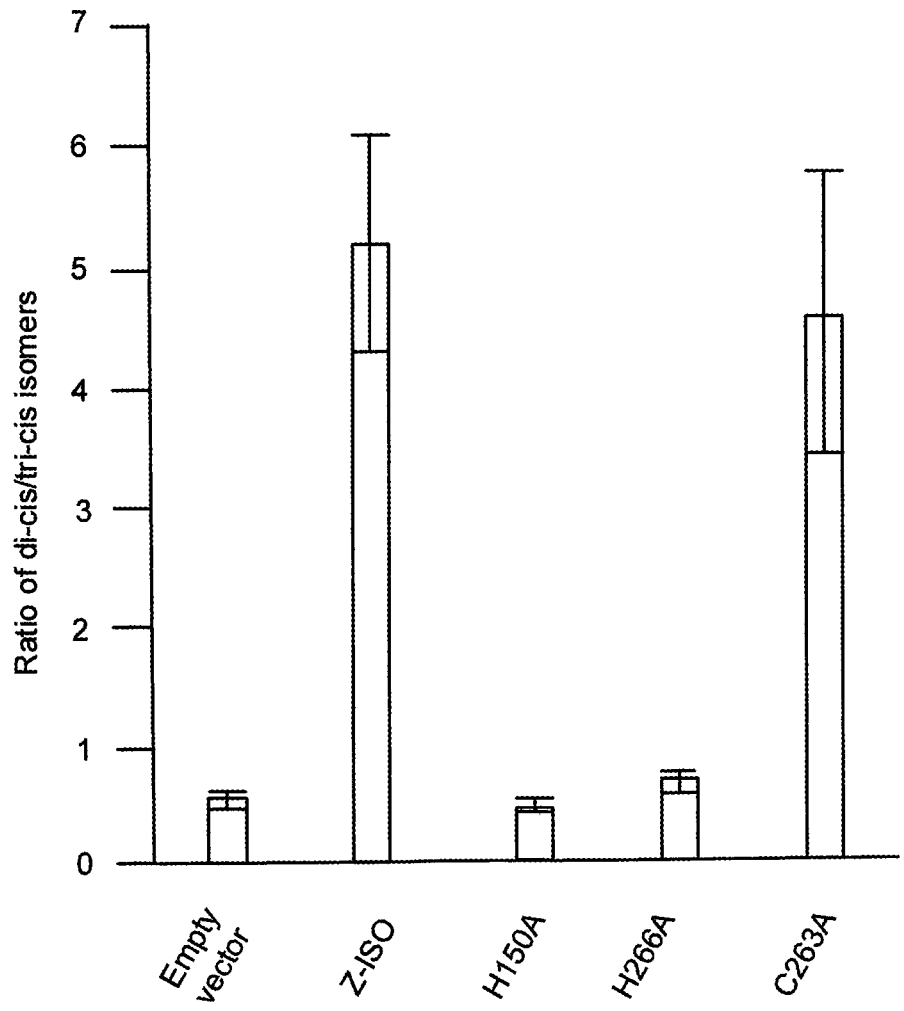
FIG. 5A is a graph depicting isomerization activity, tested by functional complementation in E. coli, with carotenoid products measured by HPLC.
Figure 5B:
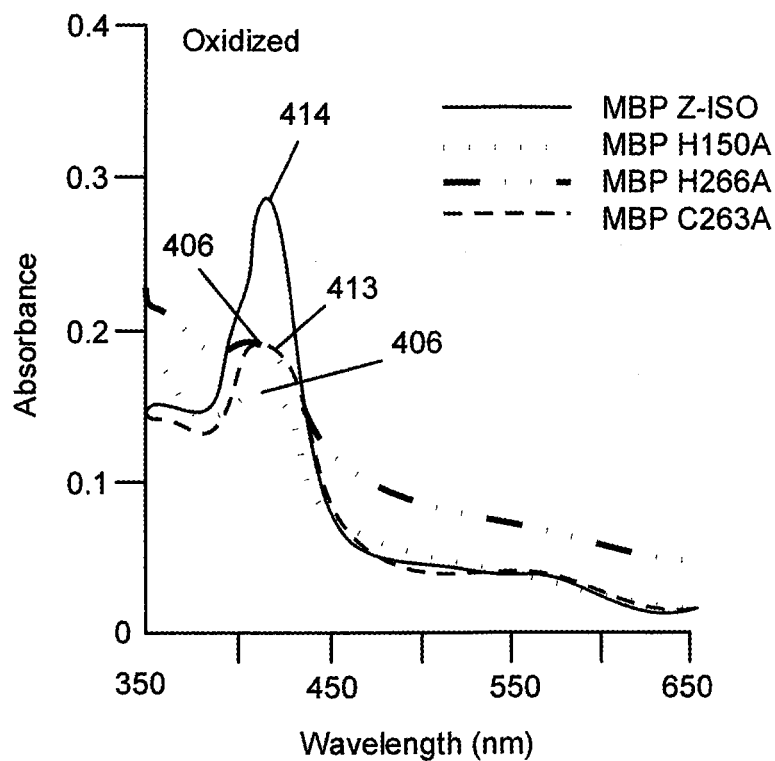
FIG. 5B and FIG. 5C are UV-vis spectra normalized for absorbance at 280 nm for extracted mutant fusion proteins, which were as purified (oxidized) or dithionite reduced.
Figure 5C:
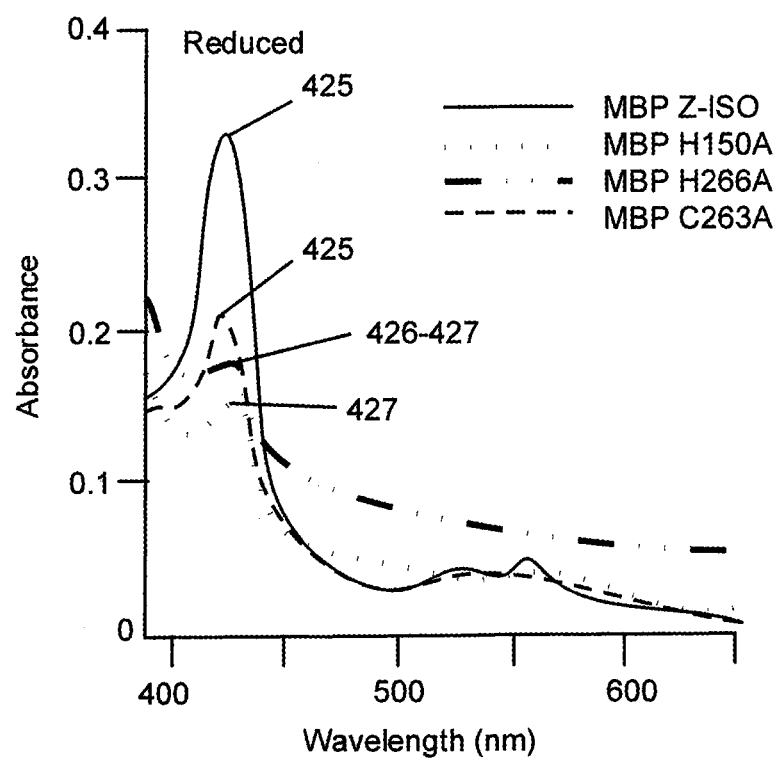
Figure 14:
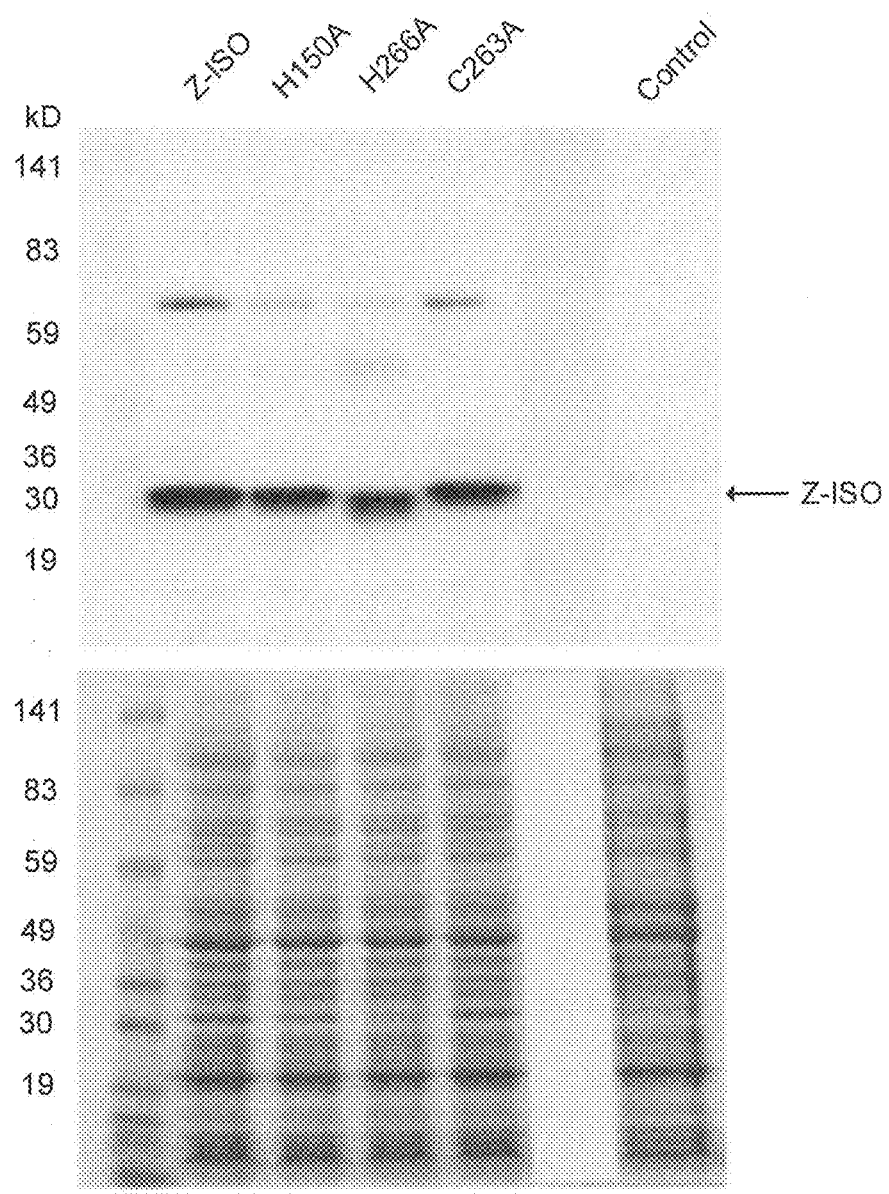
FIG. 14 depicts gels that show the immunodetection of Z-ISO and Z-ISO variants (without transit peptide)

If two heme centers exist, there should be two separate proximal histidines. To distinguish between these alternate hypotheses, another approach was used to identify all histidines in Z-ISO that could serve as heme ligands. A search was conducted for the specific residues that might function as Z-ISO heme ligands. Available Z-ISO sequences were aligned and all evolutionarily conserved residues were identified that have been reported to serve as heme ligands. These were mutagenized to alanine and tested for activity with E. coli complementation. Of all conserved histidines, only two (H150 and H266) were required for activity (FIG. 5A, Table 2). Mutants with alanine substitution at H150 (H150A) or H266 (H266A), as compared to wild-type Z-ISO, decreased the conversion of substrate to product (FIG. 14). Loss of the isomerization activity was not due to absence of expression, the possibility of which was ruled out with an anti-maize Z-ISO polyclonal antiserum. Loss of either residue also disrupted heme binding, as evidenced by the reduction in bound heme for MBP-fusion proteins carrying the alanine variants and by the UV-vis spectral shift seen for both the as-purified (oxidized) or dithionite-reduced proteins (FIG. 5B and FIG. 5C). Peak maxima are listed in Table 3.

TABLE 3

Peak maxima (nm) from UV-Vis of Z-ISO and variants regarding FIG. 5.

| Protein | Oxidized | | Reduced | |
|---|---|---|---|---|
| Z-ISO | 414 | 425 | 530 | 559 |
| H150A | 406 | 427 | 525-528 | 560 |
| H266A | 406 | 426-427 | 519 | 560 |
| C263A | 413 | 425 | 530 | 559 |

Figure 6A:
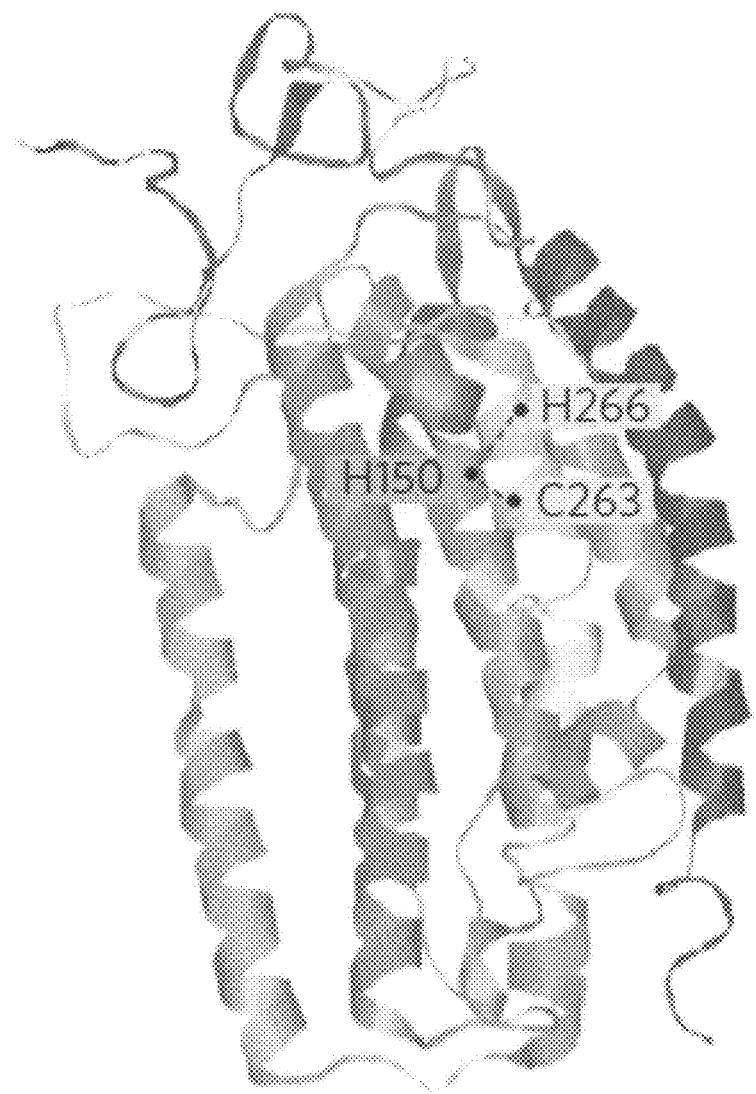
FIG. 6A is a Z-ISO homology model illustrating how proximity of alternate heme ligands predicts feasibility of distal-ligand switching between H266 and C263 when heme proximal ligand is H150.
Figure 6B:
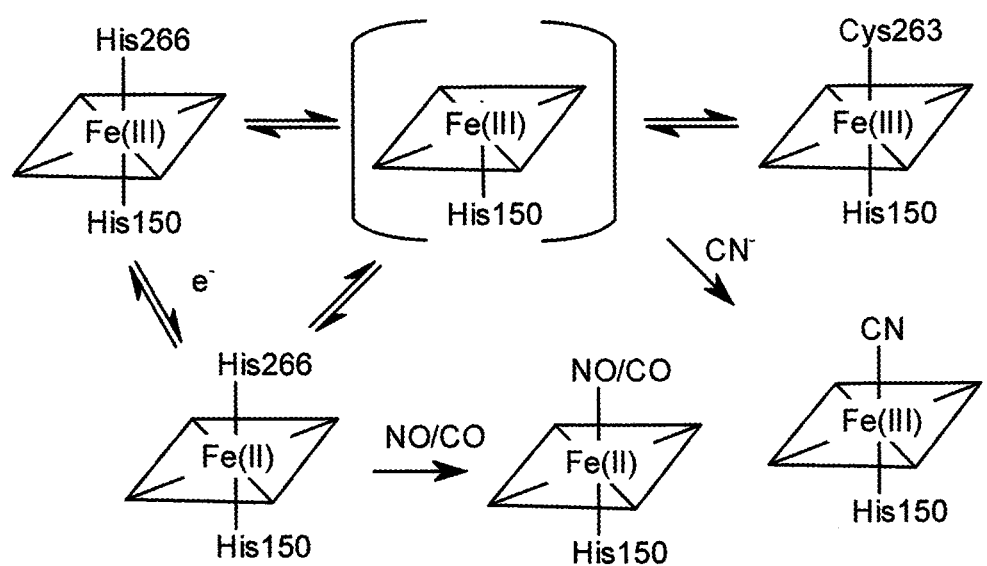
FIG. 6B is a schematic of heme-ligand states based on experimental evidence.

On the basis of the mutagenesis results, the two-heme model for Z-ISO was ruled out. Two hemes would have necessitated a total of at least three histidines (two proximal and at least one distal), but no additional conserved histidines that were required for activity beyond H150 and H266 (Table 2). Predicted locations of H150 and H266 from the Z-ISO homology model (FIG. 6A) are consistent with coordination of a common cofactor. Therefore the data are consistent with the presence of a single heme that undergoes a change in axial ligation when reduced (FIG. 6B).

The ability of Z-ISO to bind exogenous ligands indicates the availability of an axial coordination site on its heme and facile dissociation of one of two axial ligands. The most extensive dissociation takes place in the reduced, active form of the enzyme. Z-ISO activity is predicated on the heme ligands H150 and H266 and on the heme iron being in the reduced state. Therefore, it is possible that the heme iron directly mediates isomerization by interacting with the substrate. An alternative hypothesis is that, as a result of redox-dependent ligand switching, the switch to bis-histidine exposes C263, which becomes accessible to mediate catalysis. A precedent for function of a cysteine residue in catalysis, particularly in double-bond isomerization, has been seen for isopentenyl diphosphate isomerase, a non-heme enzyme that catalyzes double-bond isomerization. The C263 alternate heme ligand is the only cysteine in Z-ISO, and it is evolutionarily conserved in all Z-ISO sequences. The cysteine residue appears unlikely to function in protein dimerization, because the in vitro reaction included the reducing agent dithiothreitol, which would eliminate dimerization mediated by cysteine sulfhydryl bridges. If C263 is essential for catalysis, then mutagenesis to a nonredox active residue should inactivate the enzyme. Mutation to alanine had no effect on activity or expression when the *E. coli* complementation system was used (FIG. 5A, FIG. 14). Although the C263A MBP-fusion variant carries a reduced amount of heme equivalent to the H266A variant, the UV-vis spectrum of C263A is similar to that of wild-type Z-ISO (FIG. 5B and FIG. 5C and Table 3). When taken together, these results suggest that C263 is not catalytic but instead has a role in heme binding and reversible heme ligation.

Figure 13:
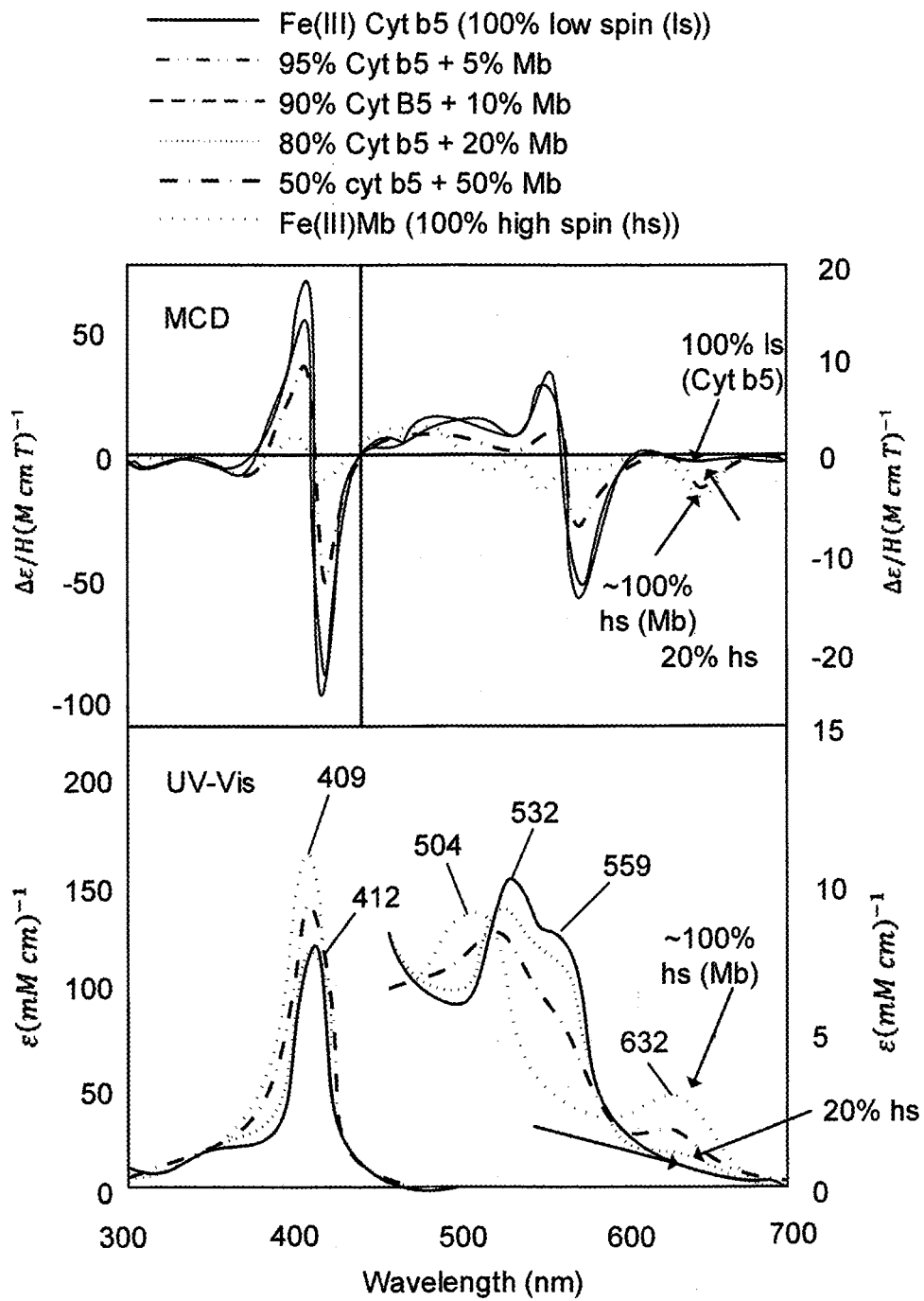
FIG. 13 is a graph showing MCD calibration of detection limits for high-spin heme. MCD and UV-Vis calibration spectra for low spin (ls, Cyt. B5)/high spin (hs, Mb) states of ferric [Fe(III)] heme proteins. From this figure it is estimated that Z-ISO contains greater than 80% low spin heme.

The heme is likely to function as the mechanistic cofactor according to the observations that, with loss of either of the apparent histidine ligands (H150 or H266), Z-ISO becomes inactive, the heme spectrum is altered, and heme binding is decreased. EPR and MCD spectroscopy together identify the axial ligands as bis-histidine or histidine-cysteine. Notably, H266 and C263 are only three residues apart. Therefore, these two residues are probably the labile ligands that can exchange with each other in the ferric state, whereas H150 is the tightly associated proximal ligand that always remains bound to the heme regardless of different redox or binding events (FIG. 6A and FIG. 6B). EPR spectra show a small amount of histidine-ligated, pentacoordinate, high-spin heme, a possible intermediate during the ligand exchange. The presence of this high-spin species with a coordination vacancy, in equilibrium with the two different hexacoordinate ligation states of the low-spin heme, is consistent with the observation that cyanide can bind to the ferric heme of Z-ISO. Furthermore, the substoichiometric binding of cyanide is consistent with the MCD calibration data (FIG. 13) showing that the pentacoordinate, high-spin species is likely to be less than 10-20% of the total heme. When Z-ISO is reduced to the Fe(II) form, the heme ligand set becomes solely bis-histidine, thus suggesting a redox-dependent ligand switch. It is this reduced form that is active in vitro. The Fe(II) heme can bind NO and CO, which can be used as a diagnostic probe to experimentally interrogate the heme for available coordination sites needed to coordinate an exogenous ligand (FIG. 6B).

The Z-ISO has therefore been shown to be an integral membrane isomerase that responds to redox state in performing a key step in carotenoid biosynthesis. Isomerization is dependent on a unique cofactor carried by Z-ISO, a heme that undergoes redox-dependent ligand switching. The reduction of the heme iron switches coordination of the heme to bis-histidine and exposes the active site for substrate binding. In the proposed mechanistic model (FIG. 6C), binding of the Z-ISO substrate displaces the weakly associated H266 ligand, and the $\pi$ electrons of the 15-15'-cis carbon-carbon double bond in the substrate serve as a Lewis base for coordination with the ferrous heme iron of Z-ISO. There is a precedent for coordination between a carbon-carbon double-bond moiety and a heme iron, as reported for a bacterial flavohemoglobin. Spectroscopic evidence provides support for coordinate bonding between the iron of the histidine-coordinated heme and a carbon-carbon double bond of an unsaturated lipid. Binding to a transition metal such as iron can reduce the bond order of an alkene because the $\pi$ electrons are delocalized into an empty orbital on the metal. As a result of direct coordination between the ferrous heme iron of Z-ISO and the target double bond in the substrate, the single $\sigma$ bond remaining in the substrate would be free to rotate to the energetically more favorable trans configuration, thus converting 9,15,9'-cis-ζ-carotene to 9,9'-cis-ζ-carotene. As a consequence of cis-trans isomerization, the entire structure of the 40-carbon ζ-carotene substrate would change from a bulky W shape to a streamlined linear shape (FIG. 1A). These cis and trans geometrical isomers would interact uniquely with the microenvironment of the Z-ISO protein structure and contribute distinctly to membrane-lipid fluidity. Therefore, the altered carotenoid structure is predicted drive release of the product from Z-ISO, thus allowing further enzymatic conversions of the Z-ISO product by downstream enzymes. Notably, according to hard-soft acid-base theory, Fe(II), in comparison to Fe(III), is a soft Lewis acid and thereby prefers ligation to soft Lewis bases. Given that the Z-ISO substrate is a soft Lewis base, the ferrous state of Z-ISO is anticipated to present superior binding kinetics and reactivity compared to the ferric state. In addition, coordination of the carotenoid double bond to the Fe(II) ion of the reduced Z-ISO heme forms a stable 18-electron coordination complex. In contrast, an unsaturated and less stable (17-electron) coordination complex is generated if the substrate were coordinating electrons with the Fe(III) ion present in the as-purified Z-ISO heme. Thus, other than the aforementioned redox-dependent conformational changes, the hard-soft acid-base analysis and the 18-electron rule in organometallic chemistry further explain the molecular basis for redox control of the isomerization activity of Z-ISO.

Heme-dependent carbon-carbon double-bond isomerization is rarely reported in the literature. The only other double-bond isomerase known to use heme as a cofactor is a bacterial cis-trans fatty-acid isomerase (CTI). CTI is a periplasmic enzyme that uses a c-type heme to perform a similar cis-trans isomerization of a double bond. However, little is known regarding the electronic structure or ligand-coordination state of the heme iron in this enzyme. The hypothesized catalytic mechanism of CTI is distinct from that of Z-ISO. It has been proposed that CTI functions in the oxidized ferric state and that the isomerization reaction is triggered by single-electron transfer from the double bond to the heme iron, thus oxidizing the double bond to a single bond.

The data show that reduction of the Z-ISO heme iron from Fe(III) to Fe(II) is necessary for enzyme activity. The heme reduction causes a ligand switch to bis-histidine and possibly triggers additional conformational changes at the active site of Z-ISO to allow substrate binding. In the resting ferric state, Z—ISO is postulated to be in a closed conformation excluding the binding of the bulky substrate (FIG. 1A). Such redox-dependent ligand-switch phenomena have been observed in many other hemoproteins, and the purpose of the ligand-switch behavior is to induce conformational changes that drive functional activation. This strategy appears to be a common natural approach to control the functional activity of hemoproteins through redox changes. For example, cytochrome cdi, nitrite reductase must be reduced to become catalytically active through a mechanism that involves a redox-mediated heme-iron ligand switch. Upon reduction, a tyrosine ligand of the $d_1$, heme in that enzyme is displaced to generate a coordinate vacancy for substrate binding. Similarly, the CO gas-sensing transcription factor CooA contains a heme cofactor that undergoes a ligand switch to make CooA competent for DNA binding. Like Z-ISO, CooA goes through a redox-mediated ligand switch upon reduction of the heme iron: a cysteine axial ligand is replaced by a histidine, thus enabling the binding of CO to the heme iron at the ferrous state via displacement of the relatively weakly bound histidine ligand. Conformational changes then follow to drive DNA binding. Another example is bacterial di-heme cyto-chrome c peroxidase (bCcP). In the resting di-ferric state of bCcPs, one heme has a bis-histidin e axial ligand set, and the other heme has a histidine-methionine axial ligand set. The two hemes are over 14 Å apart. A reductive activation process is generally needed for the proper function of bCcPs: single-electron reduction of the high-potential histidine-methionine heme triggers a series of conformational changes that remotely displace one of the histidine ligands of the other heme, thus allowing the access of the cosubstrate, $H_2O_2$, to that site. Notably, a common feature of these examples is that reduction of the inactive ferric form generates the active ferrous form, and the ligand switch, as well as associated conformational changes, enables the binding of substrate via the creation of a coordinate vacancy, a weakly associated ligand or a binding cavity. This strategy can effectively protect the heme cofactor from nonproductive binding events and thereby avoids undesired side reactions.

Because the activity of Z-ISO is controlled by redox state, plastid physiology and stress affect Z-ISO and downstream flux through the carotenoid pathway are impacted. Plastids undergo dramatic shifts in redox status as a result of photosynthetic activity in the light and nonphotosynthetic activity in the dark. Changes in redox status are known to be reflected through dynamic control of metabolism. For example, redox modulators (such as ferrodoxins and thioredoxins) adjust heme- and chlorophyll-biosynthetic activity in response to varying redox state. It has been proposed that carotenoid biosynthesis is also under redox control, although most of the molecular details are unknown. Mutations that inhibit expression of Z-ISO are already known to block production of carotenoid-pathway end products. On the basis of the results presented in this disclosure, changes in plastid redox state are predicted directly influence Z-ISO activity and consequentially alter flux in the carotenoid-biosynthetic pathway. Redox tuning of Z-ISO activity could position Z-ISO as a gatekeeper for dynamic control of carotenogenesis on short time scales. That is, carotenoid pools could be rapidly adjusted by redox tuning of Z-ISO to respond to variable needs for photosynthesis and signaling pathways related to stress and development.

Stress is a known factor affecting biosynthesis and action of carotenoids and their derivatives. NO is known to be produced directly at the site of carotenoid biosynthesis in plant plastids in response to stress and has been shown to inhibit carotenoid accumulation. In addition, NO is known to inhibit heme enzymes through binding to the heme iron, especially the ferrous form. The ability of Z-ISO to bind NO, tested in the laboratory as a diagnostic heme-ligand probe, suggests that Z-ISO could be regulated by NO in vivo.

Hemoproteins possess a wide range of biological functions, acting as enzymes, electron transporters, gas sensors, gas transporters and transcription factors, but double-bond isomerization is not generally considered to be a prototype activity for hemoproteins. Z-ISO is the only known heme-dependent isomerase that uses a ferrous iron, undergoes redox-mediated ligand switching and performs isomerization of a long hydrocarbon in a membrane environment. Therefore, studies of Z-ISO as presented here open the path for further discovery and understanding of a new class of hemoenzymes that perform double-bond isomerization in hydro-phobic environments. In the case of Z-ISO, isomerization is critical for mediating metabolic flux of a vital plant pathway that is also important for nutrition of humans and other animals. Further understanding of Z-ISO function will provide opportunities to better control carotenoid biosynthesis and facilitate breeding of more-resilient plants in a changing climate and production of more-nutritious crops.

Methods

General gene cloning. All gene constructs were verified by DNA sequencing.

Z-ISO expression and purification. Cloning. The maize Z-ISO coding sequence with transit sequence was commercially synthesized (Genscripl) to be codon optimized for *E. coli*, and restriction sites were added for cloning into SacI and BamHI sites of pUCS7 (FIG. 15). The final construct was named ZmZISO ACA-less (no. 516). From this clone, the sequence encoding Z-ISO beginning at residue 49 was PCR amplified with primers tacttccaatccaatgc-catgCGTCCGGCGCGTGCGGTGG (forward, SEQ ID NO: 1) and TTATCCACTTCCAATGCTACCAGG-GAAGTTGGTAGCTG (reverse, SEQ ID NO: 2) and inserted by ligation-independent cloning into pMCSG9-$His_{10}$ (no. 646). Primer sequences in lowercase letters were for ligation-independent cloning, and those in uppercase were gene specific. The resulting construct, pMCSG9 Z-ISO E2 (no. 582), encodes a MBP::Z-ISO fusion protein consisting of a decahistidine ($His_{10}$)-tagged MBP, at the N terminus, which is separated from the C-terminal Z-ISO by a TEV protease-cleavage site. The pMCSG9-$His_{10}$ vector was produced by modification of vector pMCSG9 to have a $His_{10}$ tag instead of a hexahistidine tag and was obtained from the materials repository of the Protein Structure Initiative.

Expression and purification of the MBP::Z-ISO fusion protein. *E. coli* C43(DE3) overnight cultures containing pMCSG9 Z-ISO E2 (no. 582) were used to inoculate 2×YT medium (1% yeast extract, 1.6% tryptone and 0.5% NaCl) at 1:100 dilution. Cultures were incubated with shaking at 200 r.p.m. at 37° C. until an OD of 0.6 was reached (typically about 2 h). Protein expression was induced with 1 mM isopropyl-1-thio-D-galactopyranoside (IPTG, Gold Biotechnology) and further incubated for 16 h at 28° C. Cultures were centrifuged at 2,600 g for IS min at 4° C., and pellets were frozen until use. Pellets were resuspended (at a ratio of 50 ml per 8 g of cell pellets; about 40 ml per liter of initial culture) in resuspension buffer (50 mM Tris, pH 7.6, Sigma-Aldrich, 300 mM NaCl and 5% glycerol) containing 0.5 mM dithiothreitol (DTT, VWR), 4 µl per 25 ml benzonase (Sigma-Aldrich), 60 mg per 50 ml 4-(2-aminoethyl) benzenesulfonyl fluoride hydrochloride (AEBSF, Bio-Research Products) and 0.15 mg per ml lysozyme (Sigma-Aldrich) before sonication on ice (five times, 30 s each, at 60% power) with a Vibra Cell VC600 sonicator equipped with a 3-mm tapered microtip (Sonics & Materials). To remove unbroken cells, the preparations were centrifuged at about 15,000 g (11,000 r.p.m. in a type 45 Ti rotor) for 15 min at 4° C. To recover the membrane fraction, the supernatants were next centrifuged at about 120,000 g (32,000 r.p.m. in a type 45 Ti rotor) for 1 h at 4° C. The pellets containing cell membranes were resuspended in resuspension buffer at a ratio of 8 ml per liter of initial cell culture; this was followed by sonication as described above. After sonication, the volumes were increased for a total of 40 ml per liter of starting culture. n-dodecyl β-D-maltoside (DDM, Anatrace) was added as powder to a final concentration of 1.5%. Samples were rotated end over end at 4° C. for 15 min. Cleared lysates were incubated overnight with Ni-NTA-containing resin (Qiagen) at a ratio of 300 µl resin per 40 ml of lysate for immobilized metal affinity chromatography (IMAC) in a 5-ml polypropylene column (Qiagen). The column was washed with five resin volumes of ATP wash buffer (40 mM Tris, pH 7.6, 200 mM NaCl, 5% glycerol and 5 mM $MgCl_2$, with freshly added 5 mM ATP (Fisher Scientific), 0.1 mM DTT and 0.05% DDM (final concentrations) for 30 min, with the column under gentle rotation. A second wash (five resin volumes) with wash buffer (40 mM Tris, pH 7.6, 400 mM NaCl and 5% glycerol)

containing 0.1 mM DTT, 0.05% DDM and 30 mM histidine (Sigma-Aldrich) was performed for 5 min (with the column under gentle rotation). The MBP::Z-ISO fusion protein was eluted with elution buffer (25 mM Tris, pH 7.6, 200 mM NaCl, 200 mM histidine and 5% glycerol) containing 0.1 mM DTT and 0.05% DDM at a ratio of 1 ml elution buffer per liter of initial culture. The protein sample was then dialyzed overnight with a Slide-A-Lyzer Dialysis cassette G2 20 K membrane (Thermo Scientific) against a 1,000-fold volume of buffer containing 20 mM NaCl, 20 mM Tris, pH 7.6, 5% glycerol, 0.02% DDM and 0.1 mM DTT, at 4° C. For metal analysis, 1 mM EDTA was included in the dialysis buffer, and dialysis was done for 3 h, three times. When needed, the sample was concentrated with microconcentrators (Microcon JOO K, Amicon). For in vitro assays, protein was stored at −20° C. in buffer containing 20 mM NaCl, 20 mM Tris, pH 7.6, 40% glycerol, 0.02% DDM and 0.1 mM DTT. The yield of fusion protein was about 1 mg/liter culture at about 90% purity.

Expression and purification of NnrU. NnrU from *Agrobacterium tumefaciens* CS8 was cloned in pNYCOMPS as a C-terminal fusion to a TEV protease-cleavage site and a $His_{10}$ tag (NnrU Cl, no. 744), expressed in *E. coli* and purified as described above for Z-ISO.

Z-ISO in vitro enzyme assay. Preparation of substrate-containing liposomes. To produce the substrate, 9,15,9'-tri-cis-ζ-carotene (tri) from *E. coli* BL21(DE3) cultures, 400 ml of Luria-Bertani medium (I % tryptone, 0.5% yeast extract and 1% NaCl) containing chloramphenicol (34 μg per ml (Sigma-Aldrich)) was inoculated with 8 ml of overnight culture containing pACCRT-EBP (no. 150). Cultures were grown in the dark at 37° C., with shaking at 160 r.p.m. for 8 h before induction with 10 mM IPTG. Cultures were further incubated at 28° C., with shaking at 100 r.p.m. for 40 h and for an additional 2 d without shaking. Cells were centrifuged at 2,600 g, and pellets were resuspended in a total of 40 ml of methanol, distributed in four conical tubes with equal volumes of extract and then sonicated twice on ice (30 s each, at 60% power) with a Vibra Cell VC600 sonicator equipped with a tapered 3-mm microtip (Sonics & Materials). Extracts were centrifuged at 2,600 g for 10 min, and supernatants were transferred to 15-ml conical tubes and evaporated under nitrogen gas in the dark. Dried samples were resolubilized in 300 μl of methanol, transferred to 1.5-ml microfuge tubes, frozen at −80° C. for 1 h and centrifuged at 16,000 g at 4° C. Extractions were then combined, and 1 ml was used to prepare liposomes. Cells also accumulate 9,9'-tri-cis-ζ-carotene (di), and therefore enzymatic conversion is measured as the ratio of di to tri isomers. For preparation of liposomes, 1 ml of substrate extract (58 μM, estimated by spectroscopy, with the molar extinction coefficient for ζ-carotene, $\varepsilon_{400}$, equal to 138,000) was mixed with 35 μl of soybean L-α-phosphatidylcholine (Sigma-Aldrich, 99% pure) (20 mg per ml in methanol). The mixture was dried under $N_2$, and this was followed by addition of 800 μl sonication buffer (25 mM HEPES, pH 7.8, 100 mM NaCl and 10% glycerol) and sonication on ice with a Vibra Cell VC600 sonicator equipped with a 3-mm tapered microtip (Sonics & Materials) for 1 min, at intervals of 10 s at 20% power.

In vitro reactions. To assemble a biphasic assay system (final volume of 400 μl), purified, MBP::Z-ISO fusion protein (10 μM final concentration) was incubated with 15 μl of AcTEV protease (ISO units, Invitrogen) for 2 min at room temperature. To generate reducing conditions, freshly prepared sodium dithionite (Sigma-Aldrich, 85% pure) was added to a final concentration of 10 mM in the assay. To initiate the reaction, 200 μl of substrate-containing liposomes (for a final concentration of 36.5 μM substrate) was added, and reactions were overlaid with $N_2$ gas before capping. Reactions were incubated at 28° C. under continuous shaking at 130 r.p.m. for 3 h in the dark (to prevent photoisomerizalion). React ions in the absence of sodium dithionite were also assembled. As a negative control, heat-denatured (10 min at 100° C.) MBP::Z-ISO fusion was used. Reactions were extracted by addition of 1 ml of petroleum ether/diethyl ether 2:1 (v/v), and the organic phase was collected, dried under $N_2$ dissolved in 150 μl methanol and 100 μl and separated by HPLC as described below. All reactions were replicated three times.

Bioinformatics. MEMSAT3, which has been experimentally validated and determined to be one of the better predictors of membrane topology, was used to predict transmembrane domains in maize Z-ISO. The transit-peptide sequence was predicted with the ChloroP program as previously reported. The Z-ISO protein sequence from *Zea mays* was analyzed by the fold-recognition program, LOOPP (LOOPP parallel driver v7.0 with LOOPP v3.20) which modeled 276 residues of Z-ISO onto a di-iron protein, PDB 2INP (resulting model in FIG. 6A; alignment of the two sequences is shown in Supplementary FIG. 10 of U.S. patent application 62/168,994 the content of which is incorporated by reference).

HPLC analysis. HPLC separations were performed on a Waters HPLC system equipped with a 2695 separation module, 996 photodiode array detector (Waters) and Empower I software (Waters). A C30 Develosil 5u RPAQUEO US (250×4.6 mm) column from Phenomenex (Nomura Chemical) was used. For isocratic separation of 100 μl of carotenoid extract, a mobile phase of four parts water, 66 parts methanol (VWR, HPLC grade) and 30 parts methyl-t-butyl-ether (VWR, HPLC grade), at a constant flow rate of 1 ml per min for 80 min, was applied. Identification of ζ-carotene isomers was based on elution time and spectra, as previously published.

Z-ISO localization. Transient expression of Z-ISO in protoplasts. A full copy of maize Z-ISO without a stop codon was amplified from pColZmZ-ISOI plasmid (no. 497), with forward primer 2793 (5'-atctctagaATGGCCTCCCAGCTCCGCCTCCACC, SEQ ID NO: 3), containing an XbaI site, and reverse primer 2794 (5'-atcggatcc CCAGGGAAGTTGGTAGCTGGATGC, SEQ ID NO: 4), containing a BamHI site, and was inserted into the pUC35S-sGFP-Nos vector (digested with XbaI and BamHI), to produce the pUC35S-M-ZISO-sGFP-Nos plasmid (no. 568), which was used for transient expression. Transient expression of Z-lSO-GFP in maize green leaf protoplasts was performed.

In vitro import of Z-ISO into chloroplasts. A full copy of the maize Z-ISO gene, without a stop codon, was amplified from pColZmZ-lSOl (no. 497) with forward primer 2851 (ccacctgcaGAATTCtatggcctc, SEQ ID NO: 5), containing an EcoRI site, and reverse primer 2854 (gtcTCTAGAttat-ttttcaaattgaggatgagaccaccagggaagttggtagct, SEQ ID NO: 6)), containing a streptavid in tag and XbaI site, and was inserted into vector pTnT (Promega), which was digested with the same restriction enzymes to yield plasmid pTnT-M-ZlSO-Strep (no. 570). pTnT-M-ZISO-Strep was used as a template for in vitro protein synthesis. In vitro protein synthesis and import of Z-ISO into isolated pea chloroplasts were performed as previously described. After import, chloroplasts were treated with thermolysin (+) to remove non-specifically bound protein. Chloroplasts were also fractionated into soluble (S) and membrane (M) fractions, including envelope and thylakoid; an equal amount of the membrane fraction as in M was alkaline treated (MA) to remove peripheral membrane proteins, thus indicating that Z-ISO is a membrane integral protein. Alkaline treatment has been shown to remove loosely associated peripheral membrane proteins rather than integral membrane proteins, which remain membrane associated.

Identification of a Z-ISO complex. After [$^{35}$S] methionine-labeled Z-ISO was imported into chloroplasts, the chloroplast sample was treated with 0.5% Triton X-100 to isolate protein complexes under native conditions. The sample was then separated into individual complexes by native gel electrophoresis in a NativePAGE Novex 4-16% gel (Invitrogen, Life Technologies), according to the instructions of the manufacturer. The gel was then dried and the radioactive band detected by a Phosphorimager system (Amersham, GE Life Sciences). The size of the band was estimated in comparison to NativeMark protein marker (Invitrogen, Life Technologies).

Detection of metals in Z-ISO. Inductively coupled plasma optical emission spectrometry (ICP-OES). Samples of MBP::Z-ISO (greater than 90% pure) were dialyzed three limes each against a 1,000-fold volume of buffer (20 mM Tris, pH 7.6, 20 mM NaCl, 5% glycerol, 0.02% DDM, 0.1 mM DTT and 1 mM EDTA) and injected into a Spectro Genesis inductively coupled optical emission spectrometer to measure the concentrations of iron at 238, 204 nm and 259, 941 nm and sulfur at 180, 731 nm For 23 μM protein, 15.4 μM iron was detected. Levels of calcium, copper, nickel, magnesium, manganese, molybdenum or zinc were insignificant.

Detection of heme. Pyridine hemochrome assay. To determine whether the chromophore bound to Z-ISO was heme, a pyridine hemocrome assay was performed. Purified protein (750 μl) was mixed with 75 μl of 1 N NaOH (Fisher Scientific), 175 μl of pyridine (Sigma-Aldrich) and 2 mg of sodium dithionite. The UV-vis absorption spectrum was immediately recorded and compared with the spectrum of the initial purified sample before addition of dithionite. The presence of the Soret band at 414 nm in the ferric stale and the presence of the Sorel band (418 nm) and appearance of the α-β bands at 555 and 530 nm, respectively, in the ferrous state were used as evidence for the presence of heme.

Heme stain. Heme staining, based on heme peroxidase activity, was performed. Protein samples were separated on a NuPAGE Bis-Tris 12% polyacrylamide gel (Invitrogen). The gel was rinsed with water for 15 s and then incubated for 1 h in the dark in a solution containing 30 ml of 40 mM TMBZ (3,3,5,5'-tetramethylbenzidine, Sigma-Aldrich) in methanol; this was followed by the addition of 70 ml of 0.25 M sodium acetate, pH 5.0 (Sigma-Aldrich). Then 5 ml of 3% hydrogen peroxide was added, and samples were mixed well until a signal corresponding to the MBP Z-ISO band appeared. The gel background was removed by destaining 15 min with 3:7 isopropanol/0.25 M sodium acetate.

Binding of CN$^-$. MBP::Z-ISO, 75.46 KDa (1.58 mg per ml, 21 μM), purified as described above, was incubated with KCN (Sigma-Aldrich, greater than or equal to 96% pure) at a final concentration of 2 mM. The UV-vis spectrum was recorded before and immediately after addition and mixing of KCN. The experiment was repeated except that MBP::Z-ISO was first reduced with sodium dithionite (2 mg, added as dry powder) before addition of KCN.

UV-visible spectroscopy Z-ISO difference spectra. In the reduced minus oxidized spectrum, the graph was obtained by subtraction of the UV-vis spectrum of the dithionite-reduced enzyme from the spectrum of the enzyme as purified. In the CO difference spectrum, the graph was obtained by subtraction of the UV-vis spectrum of the dithionite-reduced enzyme from the spectrum of the enzyme that was dithionile reduced and then treated with CO. For the cyanide difference spectra, the graph was obtained by subtraction of the UV-vis spectrum of the as-purified enzyme from the spectrum of the as-purified enzyme that was treated with cyanide or by subtraction of the UV-vis spectrum of the dithionite-reduced enzyme from the spectrum of the dithionite-reduced enzyme that was treated with cyanide (FIG. 12).

Electron spin resonance spectroscopy. X-band EPR spectra of Z-ISO were recorded in the perpendicular mode on a Bruker ER200D spectrometer coupled with a 4116DM resonator at 100-kHz modulation frequency. The measurement temperature was maintained at 10 K with an ESR910 liquid-helium cryostat and an ITC503 temperature controller from Oxford Instruments. The reduced Z-ISO protein was generated by dithionate reduction under anaerobic conditions. Nitric oxide was anaerobically introduced through a gas-tight syringe to the headspace of the quartz EPR tubes containing reduced Z-ISO. An argon flush was maintained above samples to protect them from oxidation by $O_2$ and to minimize an anomalous EPR signal near g of 2, which derives from NO.

Magnetic circular dichroism. MCD spectra were measured on a Jasco J815 spectropolarimeter fitted with a Jasco MCD-1 B magnet at a magnetic-field strength of 1.41 T at 4° C. with a quartz cuvette with 0.5-cm path length and interfaced with a Silicon Solutions PC through a JASCO IF-815-2 interface unit. MCD data acquisitions and manipulations were carried out with JASCO software, as reported previously.

Site-directed mutagenesis and functional complementation in E. coli. The maize Z-ISO cDNA coding sequence from pColZmZ-ISOl plasmid (no. 497) was used as a template to PCR-amplify and subclone Z-ISO lacking the transit-peptide sequence (amino acids 1-46). For PCR, forward primer (5'-cgggatcct CACGCTCGTCCCGCCCGTGCG-3', SEQ ID NO: 7) containing a BamHI site and reverse primer (5'-gcgtcgacc-TACCAGGGAAGTTGGTAGCT-3', SEQ ID NO: 8) containing a SalI site were used. Lowercase letters in primers contain restriction sites, and uppercase letters contain gene-specific sequences. The resulting PCR product was further inserted into the BamHI and SalI sites of pCOLADuet-1, forming a histidine-tag::Z-ISO fusion, and the vector was named pCola Zm Z-ISO NTP (no. 579). pCola Z-150 NTP was then used as template to perform substitutions of conserved residues to alanine. Residue substitutions used in this study were H150 (no. 797, pCol Zm Z-ISO NTP H150A), H266 (no. 798, pCol Zm Z-ISO NTP H266A) and C263 (no. 796, pCol Zm Z-ISO NTP C263A). Other residue substitutions tested were made in the pColZmZ-ISOI plasmid (no. 497): H191 (no. 523, pCol Zm Z-ISO H 191A), H208A (no. 528, pCol Zm Z-ISO H208A), H241 (no. 529, pCol Zm Z-!SO H241A), H253 (no. 530, pCol Zm Z-ISO H253A). H354 (no. 532, pCol Zm H354A), H285 (no. 525, pCol Zm H285A) and H286A (no. 526, pCol Zm Z-ISO H286A). For H150, H266 and C263, mutations were also created in the MBP::Z-ISO fusion construct with the pMCSG9 Z-ISO E2 plasmid (no. 582) as a template to generate the MBP::Z-ISO mutant versions pMCSG9 Z-ISO E2 H150A (no. 619), pMCSG9 Z-ISO E2 H266A (no. 620) and pMCSG9 Z-ISO E2 C263A (no. 801), which were expressed in E. coli as described above. Reactions for mutagenesis were performed with the QuikChange Lightning Site-Directed Mutagenesis Kit (Stratagene) and primers designed to incorporate the desired substitution. For functional testing, the Z-ISO mutant genes were further transformed into E. coli cells containing the plasmid pAC-CRT-EBP (no. 150), which confers accumulation of ζ-carotene. For functional complementation, mutant Z-ISO genes were introduced into E. coli cells accumulating the Z-ISO substrate. Carotenoids were extracted from the bacteria containing the various enzyme variants and were subjected to HPLC analysis to quantify the ratio of product (9,9'-di-cis-ζ-carotene) to substrate (9,15,9'-tri-cis-ζ-carotene). Cells with empty vector also accumulate a small amount of product. Therefore, enzyme activity is judged by the increase over this background level. Specifically, 1-ml volumes of saturated cultures in Luria-Bertani medium (1% tryptone, 0.5% yeast extract and 1% NaCl) were added to 50 ml of fresh medium and then grown in the dark at 37° C. at 200 r.p.m. for 8 h before induction with 10 mM IPTG and further incubation for 40 h at 28° C. with slow shaking (100 r.p.m.) and an additional 2 d without shaking. For carotenoid extraction, bacterial cultures were centrifuged at 2,600 g for 10 mM. Pellets were resuspended in 5 ml of methanol containing 1% of butylated hydroxytoluene (Sigma-Aldrich, greater than or equal to 99% pure) and sonicated with a Vibra Cell VC600 sonicator equipped with a 3-mm tapered microtip (Sonics & Materials) on ice twice (30 s each, at 60% power). Extracts were centrifuged at 2,600 g for 10 min, supernatants were transferred to 15-ml conical tubes, and extracts were evaporated under nitrogen gas in the dark. Dried samples were resolubilized in 500 µl of methanol, transferred to 1.5-ml tubes, frozen at −80° C. for 1 h and centrifuged at 16,000 g at 4° C., and supernatants were used for HPLC separation as described above. Complementation experiments were replicated three times.

Immunodetection of Z-ISO. For antibody generation, 2 mg of MBP::Z-ISO protein (no. 582) was digested with TEV protease to generate free Z-ISO. Samples were separated with the NuPAGE system from Invitrogen. Protein bands corresponding to Z-ISO were excised and shipped to Lampire Biological Laboratories for rabbit immunization. Polyclonal antibodies against Z-ISO were generated in two rabbits identified as no. 190202 and no. 190203. For immunodetection, protein samples were separated by electrophoresis with the NuPAGE system (Invitrogen). Reducing conditions in the samples were generated with DTT (100 mM). Proteins were transferred onto nitrocellulose membranes (Optitran, Whatman) with an electrophoretic transfer cell (Criterion Blotter, Bio-Rad) at 20 V overnight, ° C. with Ix transfer buffer (25 mM Tris, 192 mM glycine and 20% (v/v) methanol). The membranes were then incubated in blocking buffer (1×PBS buffer (137 mM NaCl, 2.7 mM KCl, 8 mM $Na_2HPO_4$, and 2 mM $KH_2PO_4$), 3% bovine serum albumin (Fisher Scientific) and 1% Tween-20 (Sigma-Aldrich)) for 1 h at room temperature, then for 1 h at room temperature with anti-Z-150 polyclonal antibody (1:2,000) produced in rabbit no. 190203. After washing, the membranes were incubated with horseradish peroxidase-conjugated goat anti-rabbit IgG (Invitrogen) for 1 h at RT and washed with 1×PBS buffer containing 1% Tween-20 for 15 min; this was followed by four additional washes of 5 min each. Immunoreactions were visualized with the Super Signal West Dura kit (Thermo Scientific). Fluorescence signals were captured with a G:box (ChemiXT4) from Syngene with Genesys V1.3.1.0 software.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for isomerizing a double bond, the method comprising:
   exposing an isoprenoid substrate to an isomerase enzyme, wherein the isoprenoid substrate comprises a conjugated double bond system with at least three double bonds including a central double bond and the isomerase enzyme comprises a redox-regulated ligand switch and heme b cofactor, wherein the heme b cofactor comprises an iron having an iron (III) oxidation state and the central double bond has cis stereochemistry, wherein the isomerase enzyme comprises SEQ ID NO: 12;
   exposing the isomerase enzyme to a reducing agent such that the isomerase enzyme changes from the iron (III) oxidation state to an iron (II) oxidation state, wherein the isomerase enzyme isomerizes the central double bond when in the iron (II) oxidation state and does not isomerize the central double bond when in the iron (III) oxidation state; and
   permitting the central double bond in the substrate to undergo isomerization from the cis stereochemistry to a trans stereochemistry, wherein the isomerization is catalyzed by the isomerase enzyme.

2. A method for isomerizing a double bond, the method comprising:
   exposing an isoprenoid substrate to an isomerase enzyme, wherein the isoprenoid substrate comprises a conjugated double bond system with at least three double bonds including a central double bond and the isomerase enzyme comprises a redox-regulated ligand switch and heme b cofactor, wherein the heme b cofactor comprises an iron having an iron (III) oxidation state and the central double bond has cis stereochemistry, wherein the isomerase enzyme consists of SEQ ID NO: 12;
   exposing the isomerase enzyme to a reducing agent such that the isomerase enzyme changes from the iron (III) oxidation state to an iron (II) oxidation state, wherein the isomerase enzyme isomerizes the central double bond when in the iron (II) oxidation state and does not isomerize the central double bond when in the iron (III) oxidation state; and
   permitting the central double bond in the substrate to undergo isomerization from the cis stereochemistry to a trans stereochemistry, wherein the isomerization is catalyzed by the isomerase enzyme.

* * * * *